(12) United States Patent
Aharonowiz et al.

(10) Patent No.: US 9,862,925 B2
(45) Date of Patent: Jan. 9, 2018

(54) HUMAN STEM CELL-DERIVED NEURAL PRECURSORS FOR TREATMENT OF AUTOIMMUNE DISEASES OF THE CENTRAL NERVOUS SYSTEM

(75) Inventors: Michal Aharonowiz, Modiin (IL); Ofira Einstein, Modiin (IL); Benjamin Reubinoff, Doar Na Haela (IL); Tamir Ben-Hur, Jerusalem (IL)

(73) Assignee: Hadasit Medical Research Services & Development Limited, Jerusalem (IL)

( * ) Notice: Subject to any disclaimer, the term of this patent is extended or adjusted under 35 U.S.C. 154(b) by 622 days.

(21) Appl. No.: 12/740,496

(22) PCT Filed: Oct. 29, 2008

(86) PCT No.: PCT/IL2008/001426
§ 371 (c)(1),
(2), (4) Date: Apr. 12, 2011

(87) PCT Pub. No.: WO2009/057111
PCT Pub. Date: May 7, 2009

(65) Prior Publication Data
US 2011/0189135 A1 Aug. 4, 2011

Related U.S. Application Data

(60) Provisional application No. 61/000,746, filed on Oct. 29, 2007.

(51) Int. Cl.
*C12N 5/0797* (2010.01)
*A61K 35/30* (2015.01)
*A61K 35/12* (2015.01)

(52) U.S. Cl.
CPC ............ *C12N 5/0623* (2013.01); *A61K 35/30* (2013.01); *A61K 2035/122* (2013.01); *C12N 2501/105* (2013.01); *C12N 2501/11* (2013.01); *C12N 2501/115* (2013.01); *C12N 2501/13* (2013.01); *C12N 2501/135* (2013.01); *C12N 2501/385* (2013.01); *C12N 2501/395* (2013.01); *C12N 2501/41* (2013.01); *C12N 2501/70* (2013.01); *C12N 2506/02* (2013.01)

(58) Field of Classification Search
None
See application file for complete search history.

(56) References Cited

U.S. PATENT DOCUMENTS

2005/0095706 A1* 5/2005 Zhang et al. .................. 435/368
2005/0176626 A1* 8/2005 Goldman et al. .................. 514/8
2005/0282272 A1 12/2005 Bhatia et al.

FOREIGN PATENT DOCUMENTS

EP      2 617 809 A2    7/2013
WO      WO00159072      8/2001

OTHER PUBLICATIONS

ISR for PCT IL2008/001426, dated Jan. 4, 2010.*
Written Opinion of the ISA for PCT IL2008/001426, dated May 4, 2010.*
Shin et al., Stem Cells and Development, 16:131-141, Mar. 11, 2007.*
Wu et al., Chemistry and Biology, 11:1229-1238, Sep. 2004.*
Ying et al., Methods in Enzymology, 365:327-341, 2003.*
Chojnacki et al., J Neurosci, 24(48):10888-10899, Dec. 2004.*
Hu et al., Nature Protocold, 4(11):1614-1622, published online Oct. 15, 2009.*
Zhang et al., J Neurosci Res., 59:421-429, 2000.*
Zhang S-C, Nature Neurosci., 2:840-843, Nov. 2001.*
Reubinoff, B.E., et al., "Embryonic stem cell lines from human blastocysts: somatic differentiation in vitro." Nat Biotechnol, 2000. 18(4): p. 399-404.
Thomson, J.A., et al., "Embryonic stem cell lines derived from human blastocysts." Science, 1998. 282(5391): p. 1145-7.
Brustle, O., et al., "Embryonic stem cell-derived glial precursors: a source of myelinating transplants." Science, 1999. 285(5428): p. 754-6.
Keirstead, H.S., et al., "Human embryonic stem cell-derived oligodendrocyte progenitor cell transplants remyelinate and restore locomotion after spinal cord injury." J Neurosci, 2005. 25(19): p. 4694-705.
Liu, S., et al., "Embryonic stem cells differentiate into oligodendrocytes and myelinate in culture and after spinal cord transplantation." Proc Natl Acad Sci U S A, 2000. 97(11): p. 6126-31.
Zhang, P.L., et al., "Increased myelinating capacity of embryonic stem cell derived oligodendrocyte precursors after treatment by interleukin-6/soluble interleukin-6 receptor fusion protein." Mol Cell Neurosci, 2006. 31(3): p. 387-98.
Kang, S.M., et al., Efficient Induction of Oligodendrocytes from Human. Emblyonic Stem Cells. Stem Cells, 2006.
(Continued)

*Primary Examiner* — Kimberly A. Ballard
*Assistant Examiner* — Stacey MacFarlane
(74) *Attorney, Agent, or Firm* — Greenberg Traurig, LLP

(57) ABSTRACT

The present invention concerns the use of a population of cells comprising: (a) neural precursor cells committed to an oligodendroglial fate; (b) uncommitted neural precursor cells (c) differentiated oligodendrocytes; or (d) a combination of any one of (a) to (c) for the treatment of CNS autoimmune diseases, or for the preparation of a pharmaceutical composition for treating CNS autoimmune diseases, the population of cells being derived from human pluripotent stem cells. The invention also provides methods for obtaining such populations of cells, namely, neural precursor cells committed to an oligodendroglial fate as well as differentiated oligodendrocytes which then can be used in the treatment of CNS autoimmune diseases. A preferred autoimmune disease in the context of the present invention is multiple sclerosis where the population of cells is administered to the CNS for local treatment of the disease.

12 Claims, 12 Drawing Sheets

(56) References Cited

OTHER PUBLICATIONS

Glaser, T., et al., Generation of purified oligodendrocyte progenitors from embryonic stem cells. FASEB J, 2005. 19(1): p. 112-4.

Perez-Bouza, A., T. Glaser, and O. Brustle, "ES cell-derived glial precursors contribute to remyelination in acutely demyelinated spinal cord lesions." Brain Pathol, 2005. 15(3): p. 208-16.

Nistor, G.I., et al., "Human embryonic stem cells differentiate into oligodendrocytes in high purity and myelinate after spinal cord transplantation." Glia, 2005. 49(3): p. 385-96.

Einstein, O., et al., "Transplanted neural precursor cells reduce brain inflammation to attenuate chronic experimental autoimmune encephalomyelitis." Exp Neurol, 2006. 198(2): p. 275-84.

Einstein O., et al .,"Neural precursors attenuate autohnmune encephalomyelitis by peripheral immunosuppression." Ann Neurol (2007). 61: p. 209-218.

Pluchino, S., et al., "Neurosphere-derived multipotent precursors promote neuroprotection by an immunomodulatory mechanism." Nature, 2005. 436(7048): p. 266-71.

Pluchino, S., et al., "Injection of adult neurospheres induces recovery in a chronic model of multiple sclerosis." Nature, 2003. 422(6933): p. 688-94.

Shin , S., et al., "Whole genome analysis of human neural stem cells derived from embryonic stem cells and stem and progenitor cells isolated from fetal tissue." Stem cells (2007). 25(5) : p. 1298-306.

Itsykson, P., et al., "Derivation of neural precursors from human embryonic stem cells in the presence of noggin." Mol Cell Neurosci, 2005. 30(1): p. 24-36.

Ben-Dor, I., "Lentiviral vectors harboring a dual-gene system allow high and homogeneous transgene expression in selected polyclonal human embryonic stem cells." Mol Ther (2006).14: p. 255-267.

Gropp, M., et al. "Stable genetic modification of human embryonic stem cells by lentiviral vectors." Mol Ther (2003) 7:p. 281-287.

Einstein, O., et al., "Intraventricular transplantation of neural precursor cell spheres attenuates acute experimental allergic encephalomyelitis." Mol Cell Neurosci, 2003. 24(4): p. 1074-82.

Bronstein-Sitton N., et al., "Sustained exposure to bacterial antigen induces interferon-gamma dependent T cell receptor zeta down-regulation and impaired T cell function." Nat Immunol, 2003. 10: p. 957-64.

Billon, N., et al., "Normal timing of oligodendrocyte development from genetically engineered, lineage-selectable mouse ES cells." J Cell Sci, 2002. 115(Pt 18): p. 3657-65.

Joannides et al. "Human embryonic stem cell: An experimental and therapeutic resource for neurological disease" J. of Neurological Science, Vo. 265, No. 1-2, 2007, pp. 84-88.

Rice et al. "Cell therapy in demyelinating diseases" Journal of the American Society for Experimental Neurotherapeutics, Vo. 1, No. 4, 2004, pp. 415-423.

Pluchino S. et al. "The therapeutic use of stem cells for myelin repair in autoimmune demyelinating disorders" Journal of Neurological Sciences, vol. 233, No. 1-2, 2005, pp. 117-119.

Halfpenny C. et al. "Cell transplantation, myelin repair and multiple sclerosis" Lancet Neurology, vol. 1, No. 1, 2002, pp. 31-40.

Miller et al. "The promise of stem cells for neural repair" Brain Research, vol. 1091, No. 1, 2006, pp. 258-264.

Kim S et al. "Stem cell-based cell therapy in neurological diseases: a review" Journal of Neurological Research, vol. 87, No. 10, pp. 2183-2200.

Uccelli A et al. "Stem cells for multiple sclerosis: promises and reality" Regenerative Medicine, vol. 2, No. 1, 2007, pp. 7-9.

Ostenfeld T. et al. "Recent advances in stem cell neurobiology" Advances and Technical Standards in Neurosurgery, Vo. 28, 2003, pp. 12-44.

Silani et al. "Stem cells transplantation in Multiple Sclerosis: Safety and Ethics" Journal of Neurological Sciences, Vo. 265, No. 1-2, pp. 116-121.

International Search Report for International Application No. PCT/IL2008/001426 dated Jan. 4, 2010.

Zhang, Su-Chun, "Defining glial cells during CNS development", Nature Reviews/Neuroscience, vol. 2, pp. 840-843, Nov. 2001.

* cited by examiner

Figure 3G   Figure 3H

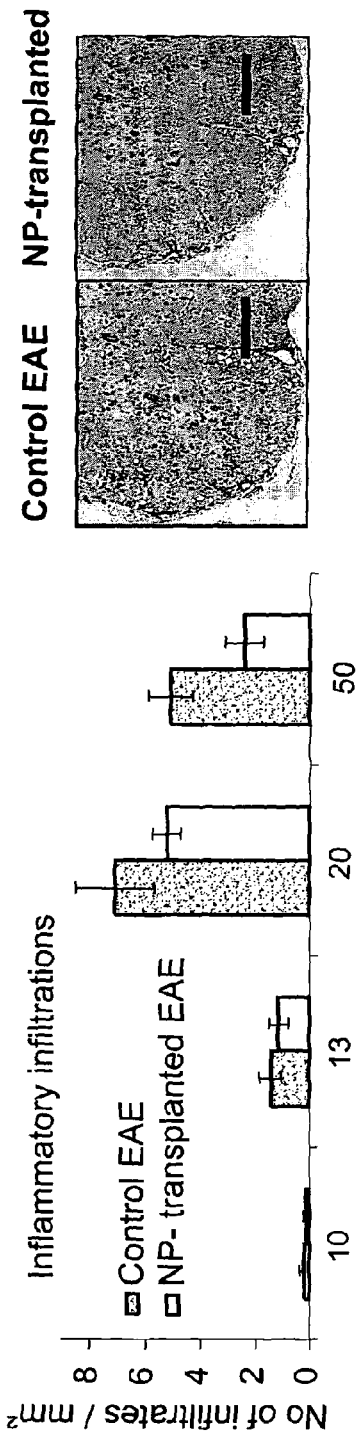
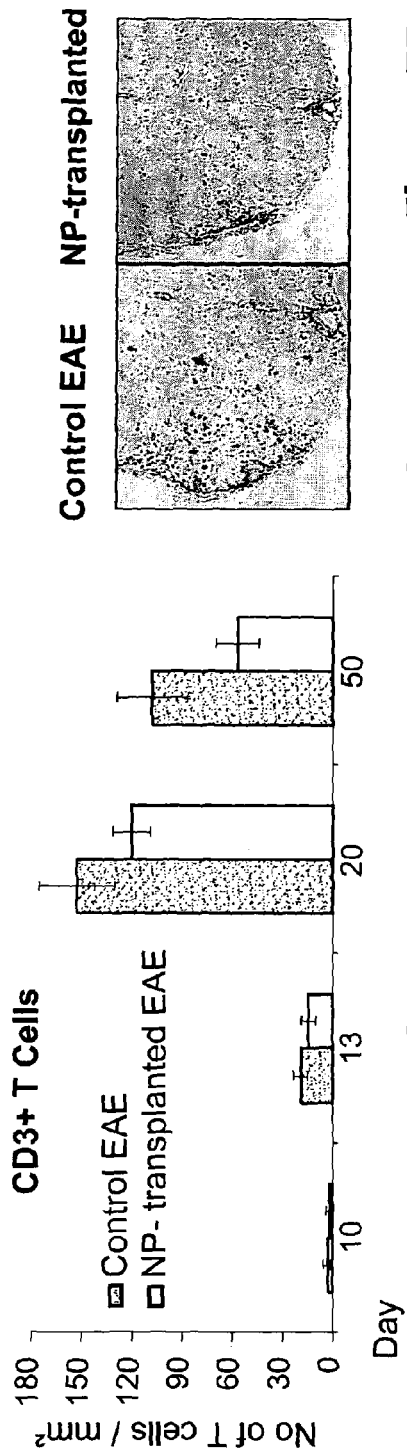
Figure 5A Figure 5B Figure 5C
Figure 5D Figure 5E Figure 5F

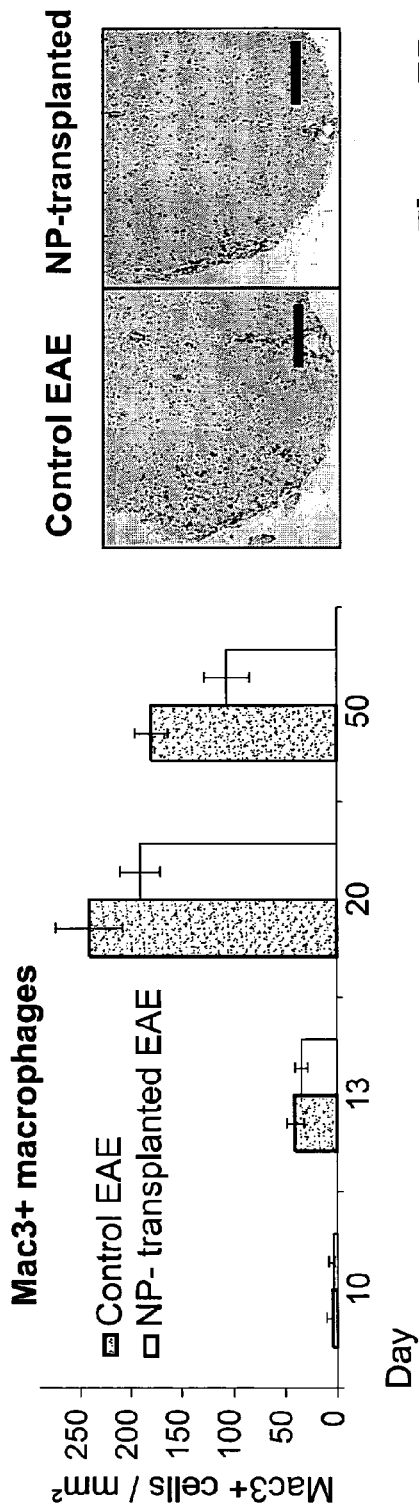
Figure 5G Figure 5H Figure 5I
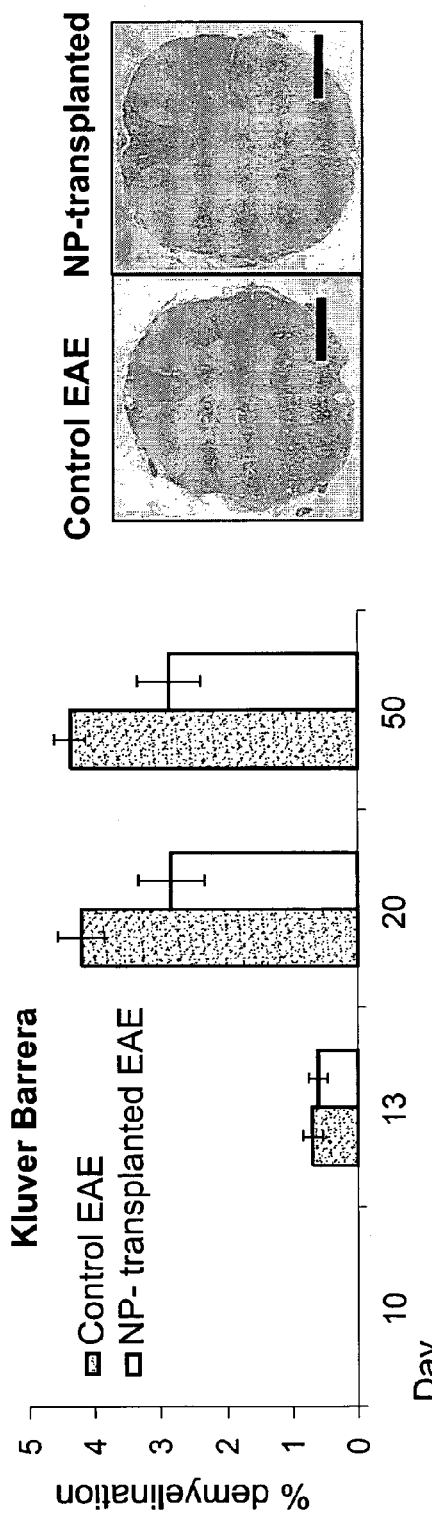
Figure 5J Figure 5K Figure 5L

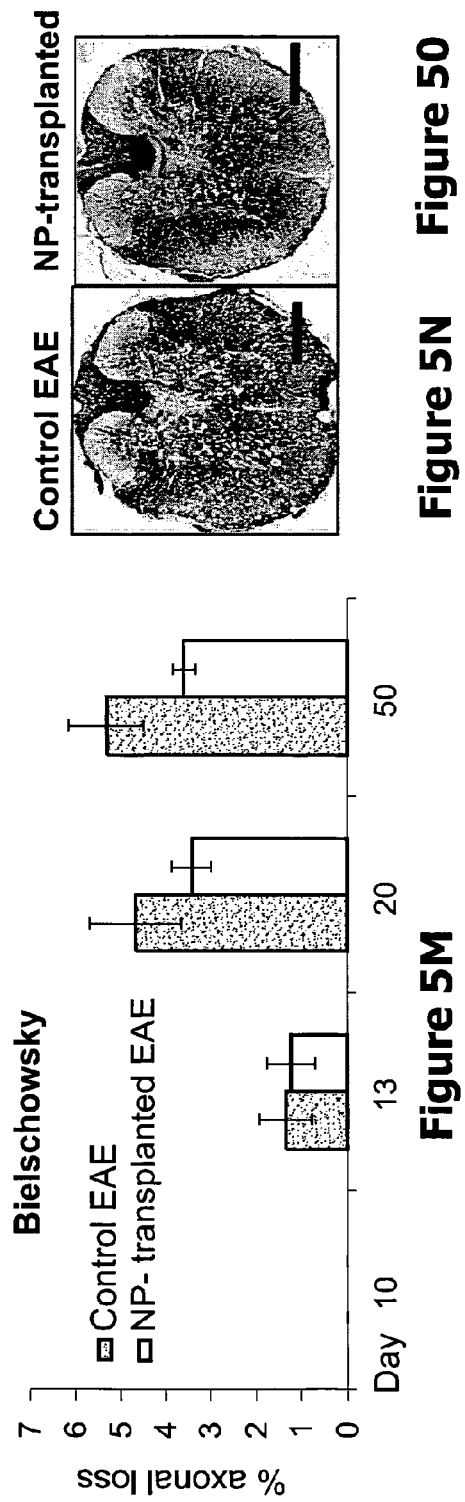
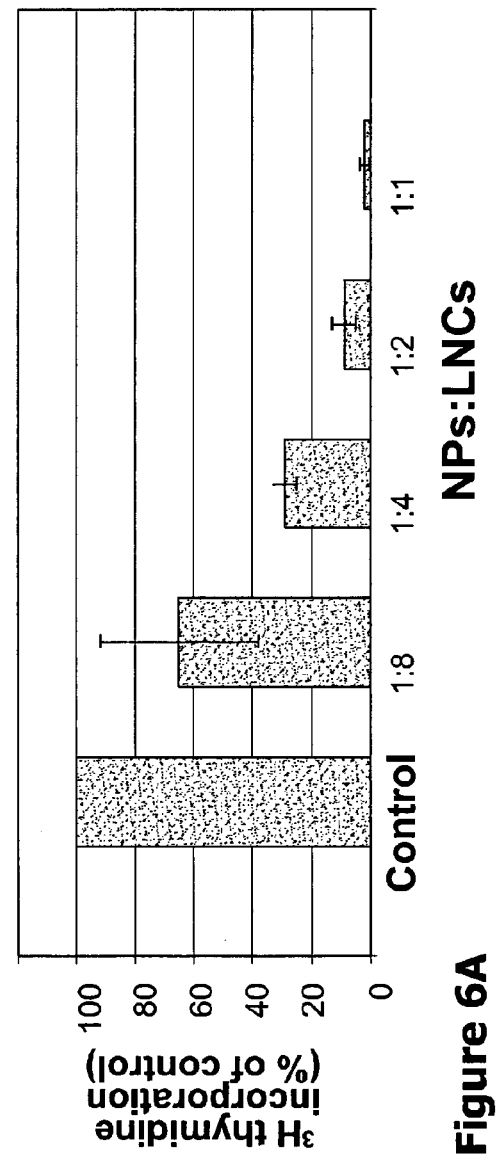
Figure 5M
Figure 5N
Figure 5O
Figure 6A

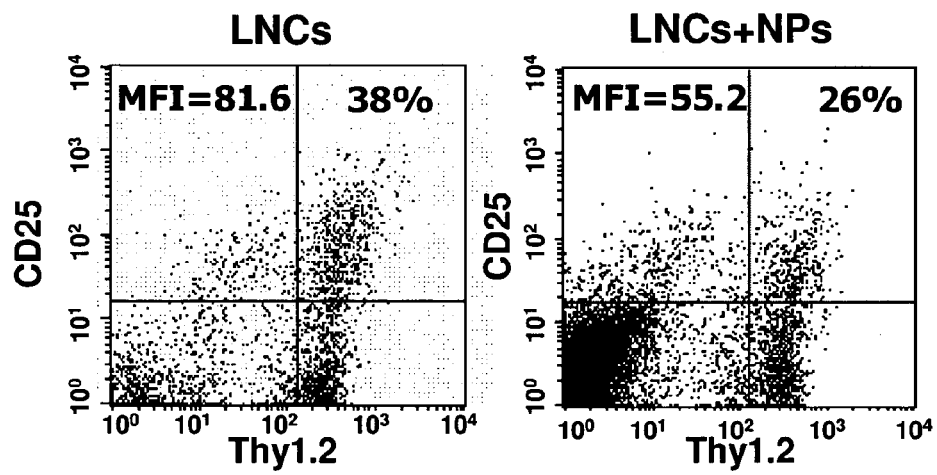
Figure 6B  Figure 6C
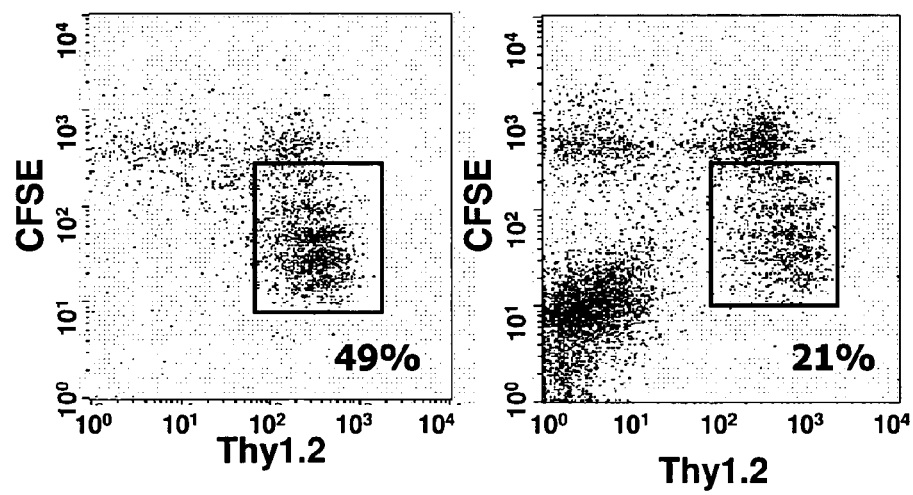
Figure 6D  Figure 6E

SEQUENCE LISTING

<160> NUMBER OF SEQ ID NOS: 1

<210> SEQ ID NO 1
<211> LENGTH: 21
<212> TYPE: PRT
<213> ORGANISM: Rattus sp.

<400> SEQUENCE: 1

Met Glu Val Gly Trp Tyr Arg Ser Pro Phe Ser Arg Val Val His Leu
1               5                   10                  15

Tyr Arg Asn Gly Lys
            20

HUMAN STEM CELL-DERIVED NEURAL PRECURSORS FOR TREATMENT OF AUTOIMMUNE DISEASES OF THE CENTRAL NERVOUS SYSTEM

This application is a national stage entry of and claims priority to Application Ser. No. PCT/IL2008/001426, filed Oct. 29, 2008; and further claims priority to U.S. Provisional Patent Application Ser. No. 61/000,746, filed with the United States Patent and Trademark Office on Oct. 29, 2007. Both applications to which priority is claimed are herein incorporated by reference for all purposes in their entirety.

FIELD OF THE INVENTION

This invention relates to cell therapy and in particular to the use of human stem cells (hESC) for the production of neural precursors for treatment of autoimmune diseases.

The following is a list of prior art which is considered to be pertinent for describing the state of the art in the field of the invention. Acknowledgement of these references herein will be made by indicating the number from their list below within brackets.

Reubinoff, B. E., et al., *Embryonic stem cell lines from human blastocysts: somatic differentiation in vitro.* Nat Biotechnol, 2000. 18(4): p. 399-404.

Thomson, J. A., et al., *Embryonic stem cell lines derived from human blastocysts.* Science, 1998. 282(5391): p. 1145-7.

Brustle, O., et al., *Embryonic stem cell-derived glial precursors: a source of myelinating transplants.* Science, 1999. 285(5428): p. 754-6.

Keirstead, H. S., et al., *Human embryonic stem cell-derived oligodendrocyte progenitor cell transplants remyelinate and restore locomotion after spinal cord injury.* J Neurosci, 2005. 25(19): p. 4694-705.

Liu, S., et al., *Embryonic stem cells differentiate into oligodendrocytes and myelinate in culture and after spinal cord transplantation.* Proc Natl Acad Sci USA, 2000. 97(11): p. 6126-31.

Zhang, P. L., et al., *Increased myelinating capacity of embryonic stem cell derived oligodendrocyte precursors after treatment by interleukin-6/soluble interleukin-6 receptor fusion protein.* Mol Cell Neurosci, 2006. 31(3): p. 387-98.

Kang, S. M., et al., *Efficient Induction of Oligodendrocytes from Human Embryonic Stem Cells.* Stem Cells, 2006. 25(2) p: 419-24

Einstein, O., et al., *Intraventricular transplantation of neural precursor cell spheres attenuates acute experimental allergic encephalomyelitis.* Mol Cell Neurosci, 2003. 24(4): p. 1074-82.

Einstein, O., et al., *Transplanted neural precursor cells reduce brain inflammation to attenuate chronic experimental autoimmune encephalomyelitis.* Exp Neurol, 2006. 198 (2): p. 275-84.

Pluchino, S., et al., *Neurosphere-derived multipotent precursors promote neuroprotection by an immunomodulatory mechanism.* Nature, 2005. 436(7048): p. 266-71.

Itsykson, P., et al., *Derivation of neural precursors from human embryonic stem cells in the presence of noggin.* Mol Cell Neurosci, 2005. 30(1): p. 24-36.

Billon, N., et al., *Normal timing of oligodendrocyte development from genetically engineered, lineage-selectable mouse ES cells.* J Cell Sci, 2002. 115(Pt 18): p. 3657-65.

Nistor, G. I., et al., *Human embryonic stem cells differentiate into oligodendrocytes in high purity and myelinate after spinal cord transplantation.* Glia, 2005. 49(3): p. 385-96.

BACKGROUND OF THE INVENTION

Multiple sclerosis (MS) is a chronic immune mediated disease of the central nervous system (CNS), which is the leading cause for neurological disability in young adults. The pathological process of MS includes immune cell infiltrations, oligodendrocyte death, demyelination and axonal damage. Several pathological and imaging studies indicate that the chronic disability is attributed mainly to axonal damage. Axonal damage in MS occurs in the early phase of the disease, in actively demyelinating lesions. In later stages of the disease, however, an ongoing, low grade axonal degeneration occurs in silent inactive plaques but not in remyelinated axons.

Spontaneous remyelination is a regular feature at early stages of lesion formation in some MS cases. Nevertheless, the remyelination process eventually fails due to environmental factors and intrinsic properties of progenitor cells.

The potential of Human embryonic stem cells (hESC) [1, 2] to differentiate into oligodendroglial cells was demonstrated both with mouse and human ES cells [3-7]. Moreover, the potential of ES cells-derived neural progeny to remyelinate in genetic models of hypo/dysmyelination and in models of focal demyelination was shown [8-11].

Transplanted cells may have a therapeutic effect in CNS autoimmune disorders not only by serving as a source of cells for regeneration, but also by immunomodulation and attenuation/abolishment of the inflammatory process. Einstein et al show that rodent fetal brain-derived neural precursor cells (NPC) transplanted into the ventricles decrease brain inflammation [12]. Similarly, peripherally injected rodent brain-derived NPC migrate into white matter and decrease brain inflammation [14]. Pluchino et al. show that intravenously injected, adult rodent brain-derived NPC, promote functional recovery in a chronic model of MS (Experimental Autoimmune Encephalomyelitis, EAE) [15]. In a later publication, Pluchino et al [14] show that adult rodent brain-derived NPC promote neuroprotection using immune-like functions, e.g. induce apoptosis of encephalitogenic T cells, exerting their effect within the CNS. Einstein et al [13] show that intravenous injection of rodent-fetal-derived NPC attenuates EAE by interacting with the peripheral immune system.

Also described is a system for regulating the immune response in the context of regenerative medicine or treatment of autoimmune disease, e.g. multiple sclerosis. The inventors propose administering undifferentiated human ES cells at the site of the pathology in an attempt to inhibit an immune response. However, since one of the inherent properties of undifferentiated ES cells is to generate tumors, this approach is probably not suitable for use in vivo, and hence immune modulation by cell therapy requires a different approach [23].

SUMMARY OF THE INVENTION

It is an object of the present invention to provide for various uses of neural precursors derived from human pluripotent stem cells for treating CNS inflammatory conditions, such as CNS autoimmune disorders.

The present disclosure is based on the finding that transplantation of hESC-derived neural precursors attenuates the clinical and pathological features of myelin oligodendrocyte glycoprotein (MOG) EAE at least by an immunosuppressive mechanism. Further it was found that after transplantation into the site of inflammation which is the CNS in EAE mice, hESC-derived neural precursors were capable of migrating and integrating in the host CNS, and differentiating towards an oligodendroglial lineage. The unique combination of therapeutic advantages of hESC-derived neural precursor cells (committed or uncommitted) and/or of differentiated oligodendrocytes propagated therefrom underlies their use as a novel form of cell therapy.

Thus, in accordance with one aspect, there is provided the use of a population of cells comprising: (a) neural precursor cells committed to an oligodendroglial fate; (b) uncommitted neural precursor cells (c) differentiated oligodendrocytes; or (d) any combinations of two or more of (a) to (c) for the treatment of CNS autoimmune diseases, said population of cells being derived from human pluripotent stem cells.

There is also provided the use of a population of cells comprising: (a) neural precursor cells committed to an oligodendroglial fate; (b) uncommitted neural precursor cells (c) differentiated oligodendrocytes; or (d) any combinations of two or more of same for the preparation of a pharmaceutical composition for the treatment of CNS autoimmune diseases, said population of cells being derived from human pluripotent stem cells.

In another aspect there is provided a method for preparing a population of neural precursor cells committed to an oligodendroglial fate; comprising:
  (a) incubating early multipotent uncommitted neural precursor cells derived from human pluripotent stem cells with RA and an HH agonist at a first concentration being between about 0.5 µM and about 2.0 µM to allow the cells to propagate as floating spheres enriched with oligodendroglial precursors;
  (b) allowing the floating spheres to further expand in a medium comprising a second concentration of HH agonist that is not more than about 0.5 µM to obtain an expanded population of neural precursor cells committed to an oligodendroglial fate.

A feature of the invention includes the use of a second concentration of HH being not more than 0.5 µM.

For the preparation of a population of cells comprising differentiated oligodendrocytes, the thus obtained expanded population of neural precursor cells committed to an oligodendroglial fate is plated on an ECM thereby allowing differentiation into said differentiated oligodendrocytes. A preferred method includes plating in the absence of HH agonist and in the absence of mitogens. A cocktail of survival and maturation factors is preferentially used, such as that detailed in the Materials and Methods.

The invention also concerns a method for treating a subject having a CNS autoimmune disease, the method comprising administering to said subject a population of cells derived from human pluripotent cells, the population of cells comprising: (a) neural precursor cells committed to an oligodendroglial fate; (b) uncommitted neural precursor cells (c) differentiated oligodendrocytes; or (d) any combination of two or more of (a) to (c).

A feature of the method of treatment concerns the local administration of the population of cells, namely, the transplantation of the cells in the CNS, specifically, to the lateral ventricles and/or intrathecally.

The invention also provides a pharmaceutical composition for the treatment of a CNS autoimmune disease, comprising a population of cells comprising: (a) neural precursor cells committed to an oligodendroglial fate; (b) uncommitted neural precursor cells (c) differentiated oligodendrocytes; or (d) a combination of any one of (a) to (c), said population of cells being derived from human pluripotent stem cells.

Yet, the invention provides a method for producing a population of differentiating neural precursor cells committed towards oligodendroglial fate, the method comprising:
  (a) incubating early multipotent uncommitted neural precursor cells derived from human pluripotent stem cells with retinoic acid (RA) and an hedgehog (HH) agonist at a first concentration between about 0.5 µM and about 2.0 µM to allow the cells to propagate as floating spheres enriched with oligodendroglial precursors;
  (b) allowing the floating spheres to further expand in a medium comprising a second concentration of HH agonist that is not more than about 0.5 µM to obtain an expanded population of neural precursor cells committed to an oligodendroglial fate.

Also provided is a method for producing a population of differentiated oligodendrocyte cells the method comprising the above steps followed by plating expanded population of neural precursor cells committed to an oligodendroglial fate on an extracellular matrix (in the absence of HH agonist or mitogens) thereby allowing differentiation into oligodendrocytes.

The invention also provides a population of oligodendroglial committed precursor cells obtainable, and preferably obtained, by incubating floating spheres of early multipotent uncommitted neural precursor cells in a medium comprising a concentration of HH agonist that is not more than about 0.5 µM; said oligodendroglial committed progenitor cells expressing one or more of the markers selected from Olig1, Olig2, NG2, PDGFRα, GD3, where at least Olig2 is co expressed with one or more of a marker selected from NG2, PDGFRα, GD3. A unique feature of these cells is that they are expandable.

Finally, there is provided a method for promoting differentiation of early multipotent uncommitted neural precursor cells towards oligodendroglial fate, the method comprising propagating floating spheres comprising early multipotent uncommitted neural precursors in a medium comprising purmorphamine.

BRIEF DESCRIPTION OF THE DRAWINGS

In order to understand the invention and to see how it may be carried out in practice, embodiments will now be described, by way of non-limiting example only, with reference to the accompanying drawings, in which:

FIGS. 3A-3J: are images showing Immunofluorescence stainings of brain sections demonstrating the survival and differentiation of transplanted neural precursors, which were identified by the expression of human mitochondria (FIGS. 3A, 3C-3G), human nuclei (FIG. 3B) and GFP (inset in FIGS. 3A, 2H). (A): The neural precursors migrated extensively into white matter areas of the CNS such as the corpus callosum (CC) and were not observed in grey areas such as subcortical grey matter (SGM). Costaining against the oligodendroglial marker, O4 (red) was used to identify the white matter. Also shown are images from transverse semi-thin sections cut from resin embedded spinal cords of transplanted (FIG. 3J) and control (FIG. 3I) animals. Arrows indicate demyelinated axons.

FIGS. 5A-5O show evolution of inflammation, demyelination and axonal damage in the CNS of hESC-derived neural precursors-transplanted versus control EAE mice exhibited by immune-cell infiltrates (FIG. 5A), T cells (FIG. 5D) and macrophages/activated microglia (FIG. 5G) Kluver Barrera staining indicative of demyelination (FIG. 5J) and Bielschowsky staining indicative of axonal damage (FIG. 5M), as well as representative images of H&E staining (FIG. 5B-5C), CD3 (FIG. 5E-5F) and Mac3 immunostaining (FIG. 5H-5I), Kluver Barrera staining (FIG. 5K-5L) and Bielschowsky silver staining (FIG. 5N-5O)

FIG. 6A-6E show suppressive effects of hESC-derived neural precursors on lymph node cells (LNCs) and T cells derived from naïve C57BL mice as exhibited by neural precursors suppression of $^3$H-thymidine incorporation into the activated LNCs (FIG. 6A), as well as by FACS analysis of interleukin-2 receptor α (IL-2Rα; CD25) expression after 24 hours of ConA-stimulation showing the inhibitory effect of human neural precursors on Thy1.2+ T cells as determined by the fraction of labeled cells and by mean fluorescent intensity (MFI) (FIGS. 6B-6C); and FACS analysis of CFSE labeled LNCs after 72 hours of ConA stimulation showing the inhibitory effect of human neural precursors on proliferation of Thy1.2+ T cells (FIGS. 6D-6E).

DETAILED DESCRIPTION OF EMBODIMENTS

The present invention stems from a sequence of empiric findings by the inventors which led to the development of novel methods and products as detailed below. Specifically, empiric data was collected concerning the effect of neural precursors derived from human embryonic stem cells (hESCs) on a chronic model of multiple sclerosis (MS), namely, EAE.

MS is the prototype of several related immune-mediated CNS diseases that are relevant to the present disclosure. The pathological process of many CNS-associated immune diseases, such as MS, involves immune cell infiltrations, oligodendrocyte death, demyelination and axonal damage. Thus, it has been envisaged by the inventors that there would be a therapeutic benefit if conditionsthat contribute to both the process of remyelination and immunosuppression are provided. Moreover, it has been envisaged by the inventors that it would be especially advantageous to deliver the effect in a targeted fashion to the involved tissue, namely, local treatment as opposed to systemic administration.

Transplantation of a population of cells derived from human pluripotent stem cells and comprising neural precursors that include oligodendroglia-committed cells and/or oligodenrocytes may be used both for suppression of the inflammatory process and thus, halting the disease progression, as well as for oligodendrocytes and myelin regeneration. The integration of such cells in host tissue and their selective migration to inflamed sites may be utilized to deliver the beneficial effect specifically to the inflamed sites of disease.

The present disclosure generally concerns the use of cells derived from human pluripotent stem cells, e.g. human embryonic stem cells (hESC) or induced pluripotent stem cells (iPS cells) for targeted (tissue-specific) suppression of inflammatory processes associated with CNS-autoimmune diseases, such as MS, as well as for in situ regeneration of oligodendrocyte population, by transplantation of the cells to the lateral ventricle or intrathecally. Thus immunosuppressive effects are combined with remyelination capabilities.

Accordingly, by a first of its aspects, the present disclosure provides the use of a population of cells comprising: (a) neural precursor cells committed to an oligodendroglial fate; (b) uncommitted neural precursor cells (c) differentiated oligodendrocytes; or (d) a combination of any one of (a) to (c) for the treatment of autoimmune diseases of the central nervous system (CNS), or for the preparation of a pharmaceutical compostion for said treatment, the population of cells being derived from human pluripotent stem cells.

Figure 1A:
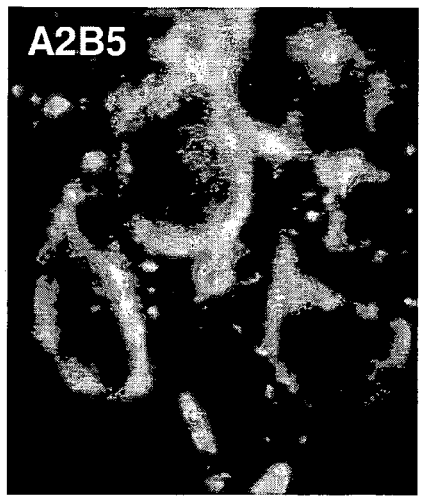
FIGS. 1A-1F are fluorescent images showing characteristics of hESC-derived neural precursors generated in accordance with the present disclosure for transplantation, the characteristics including expression of A2B5 (FIG. 1A), Musashi (FIG. 1B), Nestin (FIG. 1C) and PSA-NCAM (FIG. 1D) by over 90% of the cells, and characteristics of these cells following seven days of differentiation showing that the neural precursors differentiated mainly into βIII tubulin expressing neurons (FIG. 1E) and GFAP expressing astrocytes (FIG. 1F). Cells expressing oligodendroglial markers were not detected.
Figure 1B:
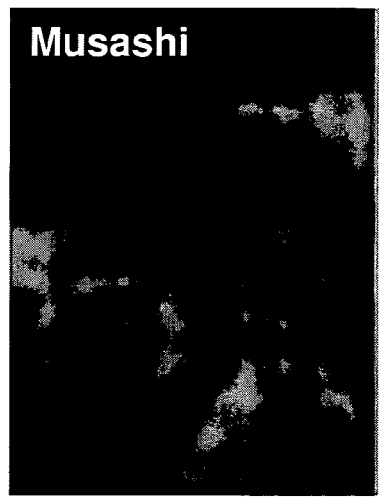
Figure 1D:
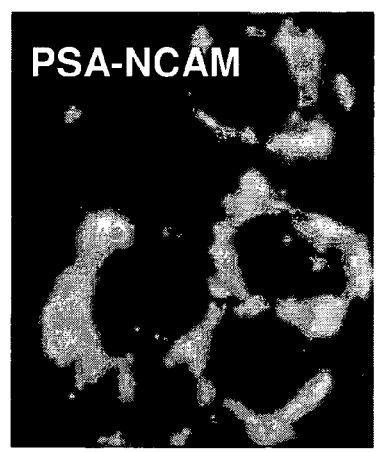
Figure 1C:
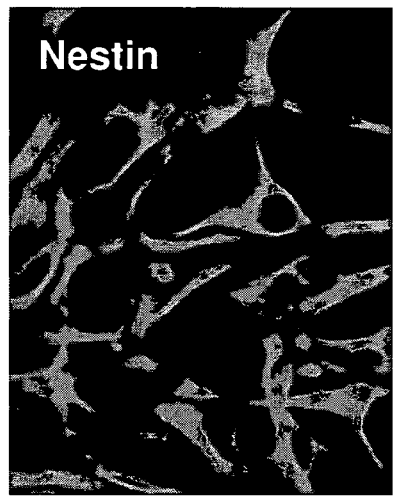

In the context of the present invention the human pluripotent stem cells include, without being limited thereto, human embryonic stem cells (hESC), human induced pluripotent stem cells (iPS cells) or any other "reprogrammed" human cell being capable of differentiating towards a desired fate, i.e. towards oligodendroglial fate The population of cells comprises uncommitted neural precursors having well defined characteristics. Such characteristics include, without being limited thereto, expression of one or more of the following markers: A2B5 (FIG. 1A), Musashi (FIG. 1B), Nestin (FIG. 1C) and PSA-NCAM (FIG. 1D) as well as the potential to differentiate into βlll tubulin expressing neurons (FIG. 1E) and GFAP expressing astrocytes. As known in the art these uncommitted neural precursors differ from the stem/progenitor cells derived from the brain of fetal tissues (16). Conditions suitable for inducing hESCs differentiation towards neural precursors are known in the art, such as from ltsykson, P., et al., (17), incorporated herein by reference. For example and without limitation, when hESCs are cultured as floating aggregates in defined medium (for example and without limitation, serum-free media supplemented with FGF-2) and BMP signalling is repressed by noggin, non-neural differentiation is suppressed, and the cell aggregates develop into spheres highly enriched for proliferating NPs. The NPs can differentiate into astrocytes, oligodendrocytes, and mature electrophysiologically functional neurons. In summary, the minimal conditions for obtaining uncommitted neural precursors from hESCs are culturing small clusters of hESCs in suspension in a chemically defined medium that promote the culture of neural precursors. Such chemically defined mediums are known in the art. The process of neutralization may be augmented by supplementation with noggin. The process of neutralization is also promoted by supplementation with FGF2 or FGF2+EGF.

When referring to a population of neural precursors derived from human pluripotent stem cells it is to be construed that at least 40%, preferably 70% and more preferably above 90% of the cells exhibit at least one characteristic of neural precursors as provided above.

The population of cells may include committed as well as uncommitted neural precursors. When referring to committed cells it is meant cells committed to an oligodendroglial fate. At times, neural precursor cells committed to an oligodendroglial fate will be referred to as oligodendroglial progenitors. The population of cells may also include (in addition or alternatively) terminally differentiated oligodendrocytes, derived from human pluripotent stem cells, as will be explained below.

In the context of the present disclosure, "cells committed to an oligodendroglial fate" are to be construed as human pluripotent stem cells that under appropriate conditions will differentiate into oligodendrocytes. Cells committed to an oligodendroglial fate have characteristics that distinguish them from uncommitted neural precursors. Such characteristics include, without being limited thereto, the oligodendroglial markers Olig1, Olig2, NG2, PDGFRα, GD3, O4, GalC and MBP.

The population of cells may be employed for the treatment of various acute and chronic CNS-autoimmune diseases that exhibits at least one inflammatory component. The diseases may include, without being limited thereto, stroke and ischemic damage to the nervous system; neural trauma (e.g., closed and penetrating injuries to the brain and spinal cord); multiple sclerosis and its variants such as neuromyelitis optica, acute disseminated encephalomyelitis (ADEM) and transverse myelitis; Guillain-Barre syndrome and its variants, acute motor axonal neuropathy, Fisher Syndrome and other immune-mediated neuropathies (e.g.,); Amyotropic Lateral Sclerosis (ALS).

The term "central nervous system" refers to all structures within the dura mater. Such structures include, but are not limited to, the brain and spinal cord.

The term "treatment" as used herein is to be construed as referring to protective treatment (i.e. prophylactice, in terms of preventing or partially preventing the CNS autoimmune disease) as well as therapeutic in terms of a partial or complete cure of the disease or adverse effect attributed to the disease. The term "treatment", as used herein, includes: (a) preventing the disease from occurring in a subject which may be predisposed to the disease but has not yet been diagnosed as having it, i.e., causing the clinical symptoms of the disease not to develop in a subject that may be predisposed to the disease but does not yet experience or display symptoms of the disease; (b) inhibiting the disease, i.e., arresting or reducing the development of the disease or its clinical symptoms; or (c) relieving the disease, i.e., causing regression of the disease and/or its symptoms or conditions.

More specifically, "treatment" in the context of the present invention is such that it would result in one or both of immunosuppressive effect and remyelination in the site of inflammation so as to prevent damage to an inflamed tissue or improve the condition of the damaged tissue. Improvement may result in the inhibition or cesation of damage caused to the damaged tissue as well as regeneration of damage already existing.

In one embodiment, the CNS autoimmune disease is associated with an inflammatory reaction, such as an inflammatory demyelinating disease. One particular disease in accordance with this embodiment is multiple sclerosis (MS).

In one embodiment, the population of cells is enriched with cells committed to an oligodendroglial fate. In the same or another embodiment, the population of cells comprises uncommitted neural precursors. In yet the same or different embodiment, the population of cells comprises cells terminally differentiated oligodendrocytes. In all embodiments, a common inventive feature is that all cells are derived from human pluripotent stem cells, preferably from human embryonic stem cells.

The population of cells comprising neural precursors committed to an oligodendroglial fate are obtainable, preferably obtained, without being limited thereto, by the following procedure:

(a) incubating early multipotent uncommitted neural precursor cells derived from human pluripotent stem cells (which, as indicated above, may be obtained as described by Itsykson, P., et al., (17) or by any other method known in the art, some of which is referred to above), with retinoic acid (RA, at a concentration of between 0.5 to 20 µM, preferably at about 1 µM) and an hedgehog (HH) agonist at an HH concentration between 0.5 µM and 2.0 µM preferably 0.5 µM, to allow said early multipotent NPs to propagate as floating spheres being enriched with oligodendroglial precursors;

(b) allowing the floating spheres to further expand in a medium comprising a second concentration of HH agonist that is not more than about 0.5 µM, preferably between about 0.2 µM and 0.5 µM, to obtain an expanded population of neural precursorcells committed to an oligodendroglial fate.

As indicated above, the population of cells may in addition or alternatively comprise differentiated oligodendrocytes. Such differentiated oligodendrocytes may be obtained by: plating the thus expanded population of cells on a culture matrix, namely, extracellular matrix (ECM), such as laminin or fibronectin, the latter being preferably, in the absence of HH agonist and mitogens, thereby allowing differentiation into said differentiated oligodendrocytes.

In one embodiment, the HH agonist, being preferably Sonic HH agonist, is selected from purmorphamine, Hh-Ag1.3 (Curis Company) and others.

In one embodiment, the incubation with HH agonist is performed in the presence of at least one mitogen. The term "mitogen" is known in the art as any chemical substance that induces cell division, i.e. triggers mitosis. Non-limiting mitogens to be used in accordance with the method disclosed herein, are bFGF and EGF or PDGF.

A surprising finding underlying the present invention is based on empiric data where hESC-derived neural precursors were administered to the target site, namely, to the lateral ventricle and the cells selectively migrated to the inflamed/damaged area. In other words, in difference with hitherto described or proposed treatments of CNS-autoimune diseases making use of stem cell derived neural precursors being administered systemically, the present disclosure has established an effective local treatment for CNS-autoimmune conditions. Those versed in the art of medicine would readily appreciate the advantages of local treatment vs. systemic treatment, at least in terms of side effects. Essentially, systemic immunosuppressive treatments render the entire body to be susceptible to infections that invaded the body or arose from the microbial flora that resides constantly in the body, as well as to malignant tumors. Here, the anti-inflammatory effects of the population of cells as defined herein are targeted specifically to the disease sites, thus avoiding any systemic complications. Targeting of cell therapy is achieved by both the direct delivery of cells to the central nervous system, as well as the nature of cells in the defined population to be attracted and to migrate towards the inflamed CNS tissue.

The present disclosure also pertains to a method for preparing a population of neural precursor cells committed to an oligodendroglial fate comprising (a) incubating early multipotent uncommitted neural precursor cells derived from human pluripotent stem cells with RA and an HH agonist at a first concentration being between about 0.5 µM and about 2.0 µM to allow the cells to propagate as floating spheres enriched with oligodendroglial precursors;

(b) allowing the floating spheres to further expand in a medium comprising a second concentration of HH agonist that is not more than about 0.5 µM to obtain an expanded population of neural precursor cells committed to an oligodendroglial fate For preparing a population of cells comprising differentiated oligodendrocytes, a further step is required, which includes plating the thus obtained expanded population of neural precursor cells committed to an oligodendroglial fate on an ECM, in the absence of HH agonist and mitogens, thereby allowing differentiation into said differentiated oligodendrocytes.

Further provided herein is a method for treating a subject having a CNS autoimmune disease, preferably those associated with an inflammatory reaction, e.g. inflammatory demyelinating disease, the method comprising administering to said subject a population of cells derived from human pluripotent stem cells as described above. The method in accordance with the present disclosure is preferably for the treatment of multiple sclerosis (MS).

The method of treatment may involve administration to a subject having a CNS-autoimmune disease with more than one population of cells derived from human pluripotent stem cells, the populations may be selected from a population of cells comprising uncommitted cells, another population comprising neural precursor cells committed to an oligodendroglial fate; and yet a further population comprising differentiated oligodendrocytes; the populations may be administered together or separately, simultaneously or in sequence (with an interval of minutes, hours or even days or weeks). The method may also include administration of a population of cells comprising a mixture of cells derived from human pluripotent stem cells selected from precursor cells committed to an oligodendroglial fate, uncommitted neural precursors, and terminally differentiated oligodendrocytes.

Treatment in accordance with the present disclosure involves, preferably, local administration (transplantation) of the population of cells in accordance with the invention to the CNS. To this end, the treatment cells may be formulated in a form suitable so or intrathecally. It has been established by empiric data, such as that presented for the first time herein, that cells derived from human pluripotent stem cells, specifically, from hESC and transplanted to the lateral ventricle migrated essentially exclusively to the inflamed site.

It is noted that the neural precursors migrate to the target site whereby they may be retained as uncommitted precursors, or committed into common bipotential neuronal/oligodendroglial precursors, or further differentiated into neuronal pogenitors, oligodendroglial-commited precursors, astrocytes, and/or mature oligodendrocytes.

The cells may be administered by various techniques known in the art of cell transplantation. These include intrathecal injection into the spinal subarachnoid space and intraventricular injection, as performed for insertion of an Omaya reservoir or a ventriculostomy, and similar methods, Treatment in accordance with the invention may include a single administration or several administrations of the populations of cells in intervals of days, weeks as well as of months. The several administrations may also include administrations of the same or different populations. For instance, one or more administrations may include a population enriched with neural precursors committed to an oligodendroglial fate, and other administrations may include terminally differentiated oligodendrocytes.

In accordance the present disclosure the amount of cells in the population to be transplanted is determined by methods known in the art of cell transplantation. The amount must be effective to at least attenuate the inflammatory response, namely to at least achieve an immunosuppressive effect on the CNS inflammatory reaction, thereby achieving improvement in the condition of the subject undergoing the treatment.

The amount will depend, inter alia, on the type and severity of the autoimmune disease to be, the site and method of administration, scheduling of administration, patient age, sex, body weight and other factors known to medical practitioners. The effective amount is typically determined in appropriately designed clinical trials (dose range studies) and the person versed in the art will know how to properly conduct such trials in order to determine the required amount.

Also provided by the present disclosure are pharmaceutical compositions for the treatment of a CNS autoimmune disease, comprising a pharmaceutically acceptable carrier and the population of NP cells derived from hESC as disclosed herein. The pharmaceutically acceptable carrier may include an ECM, such as fibronectin, laminin or any other medium required for the viability of the cells during the process of transplantation.

Also provided herein is a method for producing a population of differentiating neural precursor cells committed towards oligodendroglial fate, the method comprising:

(a) incubating early multipotent uncommitted neural precursor cells derived from human pluripotent stem cells with retinoic acid (RA) and an hedgehog (HH), the HH agonist at a first concentration between about 0.5 µM and about 2.0 µM to allow the cells to propagate as floating spheres being enriched with oligodendroglial precursors;

(b) allowing the floating spheres to further expand in a medium comprising a second concentration of HH agonist that is not more than about 0.5 µM to obtain an expanded population of neural precursor cells committed to an oligodendroglial fate.

Also provided is a method for producing a population of differentiated oligodendrocyte, comprising:

(a) incubating early multipotent uncommitted neural precursor cells derived from human pluripotent stem cells with retinoic acid (RA) and an hedgehog (HH), the HH agonist at a first concentration between about 0.5 µM and about 2.0 µM to allow the cells to propagate as floating spheres being enriched with oligodendroglial precursors;
(b) allowing the floating spheres to further expand in a medium comprising a second concentration of HH agonist that is not more than about 0.5 µM to obtain an expanded population of neural precursor cells committed to an oligodendroglial fate; and
(c) plating expanded population of neural precursor cells committed to an oligodendroglial fate on an extracellular matrix, in the absence of HH agonist and mitogens, thereby allowing differentiation into oligodendrocytes.

As used herein "differentiating cells" denotes cells that are capable of differentiating into other cell types having a particular, specialized function.

As used herein "differentiated oligodendrocytes" denotes mature cells that have fully differentiated into such cells (terminally differentiated), exhibiting the specialized function and characteristics of oligodendrocytes.

The method of producing a population of differentiating cells committed towards oligodendroglial fate or differentiated oligodendrocytes preferably makes use of the following components:
the use of HH or its agonist; where the HH agonist is preferably purmorphamine;
incubation with HH agonist is preferably, although not exclusively, performed in the presence of at least one mitogen;
the first concentration of HH agonist is preferably, although not exclusively about 0.5 µM, and the second concentration of HH agonist is between about 0.2 µM and about 0.5 µM;
the second concentration of HH agonist allows expansion of the population of oligodendroglial committed precursors.
to obtain differentiated oligodendrocytes, the committed precursor cells are plated on an ECM being preferably, but not exclusively, fibronectin in the absence of HH agonist and mitogens;

The cells obtained may be characterized by the expression of at least one of the following markers: Olig1, Olig2, NG2, PDGFRα, GD3, O4, GalC and MBP. Committed NPs to oligodendroglial fate may be characterized by the expression of Olig2 and at least one of NG2, PDGFRα, and GD3. Further, the neural precursors committed to oligodendroglial fate may be characterized by their capability to expand in the presence of low (not more than 0.5 µM) HH agonist. Differentiated oligodendrocytes are characterized by the expression of Olig2 and at least one of O4, GalC and MBP.

Also provided by the present invention is a population of oligodendroglial committed precursor cells obtainable by incubating floating spheres of early multipotent uncommitted neural precursors in a medium comprising a concentration of HH agonist that is not more than about 0.5 µM; said oligodendroglial committed precursor cells expressing one or more of the markers selected from Olig1, Olig2, NG2, PDGFRα, GD3, where at least Olig2 is co-expressed with one or more of NG2, PDGFRα, GD3. The oligodendroglial committed precursor cells can expand, under suitable conditions.

Finally, there is provided by the present invention a method for promoting differentiation of early multipotent uncommitted neural precursors towards oligodendroglial fate, the method comprising propagating for a period of at least 3 weeks, 5 weeks, 8 weeks, 12 weeks, and even 3 months, of multipotent NPs in a medium comprising purmorphamine, the cells being preferably, although not only exclusively, cultured as floating spheres. It is noted that for the first time purmorphamine is used for oligodendroglial differentiation, which allows the propagation of the committed precursor cells for such a long period of time, thus increasing the probability that the committed cells will successfully terminally differentiate into oligodendrocytes.

DESCRIPTION OF SOME NON-LIMITING EXAMPLES

Materials and Methods:

hESC culture: hESC (HES-1 cell line) with a stable normal (46XX) karyotype were cultured on human foreskin feeders in serum free medium as described (18) and were passaged weekly by treatment with collagenase IV (1 mg/ml for 20 min at 37° C).

Generation of highly enriched populations of uncommitted Neural precursors for transplantation: wild type and cloned genetically modified hESCs that were infected by a lentiviral vector expressing eGFP under the human EF1α promoter [19] were used for derivation of uncommitted neural precursors for transplantation into EAE mice.

Colonies of undifferentiated hESCs were removed from the feeders by treatment with collagenase IV (1 mg/ml for 20 min at 37° C.), transferred to 24-well culture dishes (Costar; Corning, Inc., Corning, N.Y., USA), and cultured in suspension in a chemically defined neural precursor medium (NPM) consisting of DMEM/F12 (1:1), B27 supplement (1:50), 2 mM glutamine, 50 units/ml penicillin, 50 µg/ml streptomycin (Gibco), and 20 ng/ml rh-FGF-2 (R&D Systems Inc., Minneapolis, Minn.). Recombinant mouse noggin (700 ng/ml; R&D Systems Inc.) was added to the NPM to promote neural differentiation as described [18]. After three weeks under these culture conditions the neural spheres that developed [38] were further expanded in NPM and bFGF in the absence of noggin, for 5 more weeks before transplantation.

Animals: For MOG EAE induction and transplantation experiments, 6-7 weeks old C57BL female mice were supplied by Harlan laboratories and were maintained in a specific pathogen free (SPF) unit.

MOG EAE induction: EAE was induced in 6-7 weeks old female C57B/6 mice by immunization with an emulsion containing 300 µg of purified myelin oligodendrocyte glycoprotein (MOG) peptide (SEQ ID No. 1) MEVGWYRSPFSRVVHLYRNGK, the amino acid sequence of the MOG peptide corresponding to residues 35-55) in PBS and an equal volume of complete Freund's adjuvant containing 5 mg H37RA (Difco). 0.2ml of the inoculum was injected subcutaneously at day of induction (day 0) and at day 7. In addition, 300ng of the Bordetella pertussis toxin (Sigma) in 0.2 ml PBS was injected intraperitoneally at day of induction and at day 2.

Clinical evaluations of CEAE: After CEAE induction, mice were scored daily for CEAE clinical signs, according to the following score: 0, asymptomatic; 1, partial loss of tail tonicity; 2, atonic tail; 3, hind leg weakness and/or difficulty to roll over; 4, hind leg paralysis; 5, four leg paralysis; 6, death due to EAE.

At the end of the follow-up period, the maximal score and the cumulative score of each animal were calculated. Maximal clinical score was calculated as the mean of the maximal clinical scores during the experimental period. Cumulative clinical score was calculated as the mean of the sum of the daily clinical scores during the experimental period.

Transplantation of uncommitted Neural precursors: Seven days post EAE induction (day 7) the mice were anesthetized with intraperitoneal injection of pentobarbital (0.6 mg/10 gr) and were fixed in a stereotactic device. Quantities of $5 \times 10^5$ cells or NPM in a volume of 7.5 µA were injected into each lateral ventricle.

Tissue fixation and histological preparation: For analysis of the in-vivo localization and differentiation of the transplanted cells, EAE animals were sacrificed at the end of the follow-up period (50 days post-EAE induction). For histopathological analysis of the progression of inflammation and tissue damage in the time course experiment animals were sacrificed at 10, 13, 20 and 50 days post EAE induction (n=4-5 per group on each time point). Animals were anesthetized with a lethal dose of pentobarbital and brains and spinal cords were perfused via the ascending aorta with ice-cold PBS followed by cold 4% paraformaldehyde in PBS. The tissues were dissected and post-fixed by immersion in the same fixative for 24 h at 4° C. Brains were deep frozen in liquid nitrogen and cut to serial 6-8 µM axial and longitudinal sections and spinal cords were embedded in paraffin for pathological analysis.

Pathological analysis: Analysis of inflammation, demyelination and axonal damage was performed on 5 µm paraffin-embedded serial transverse sections in three different rostrocaudal levels of the spinal cord. For histochemical analysis, sections were stained with hematoxylin and eosin, Luxol fast blue/periodic-acid Schiff staining, and Bielschowsky silver impregnation to assess inflammation, demyelination, and axonal pathology, respectively. In adjacent serial sections, immunohistochemistry was performed with antibodies against macrophages/activated microglia (rat anti-mouse Mac3, 01781D, clone M3/84; 1:200; Pharmingen, San Diego, Calif.) and T cells (rat anti-human CD3, MCA 1477; 1:400, Serotec, Bicester, United Kingdom). Primary antibodies were detected by the avidin-biotin technique using biotin conjugated secondary antibodies. The total average number of positive cells per square millimeter, in spinal cord cross sections, was counted using a grid overlay.

Apoptosis of T cells in the CNS was determined morphologically by the appearance of condensed and fragmented nuclei in CD3+ cells. The percentage of apoptotic cells was determined in transplanted and control animals (n=3 in each group) by morphological analysis of 250 CD3+ cells in random CNS sections.

Demyelination and axonal damage were assessed in spinal cord sections by calculating the area of Luxol fast blue and Bielschowsky silver staining loss, representing areas of myelin destruction and axonal loss, respectively. The percentage of demyelinated and axonal damage areas was determined by counting intersections of the grid over the demyelinated lesions and the areas of axonal loss.

For the evaluation of remyelination, animals were perfused with 4% gluteraldehyde. The fixed spinal cords were cut into 1 mm transverse blocks from the cervical, thoracic and lumbar areas. The blocks were osmicated, dehydrated through an ascending series of ethanols and embedded in TAAB resin. One µm sections were cut from each block, stained with toluidine blue (Sigma), and examined by light microscopy.

To determine whether transplantation had an effect on remyelination axons from toluidine blue stained spinal cord semi-thin sections were measured, and their G ratios were calculated (G=axon diameter/(axon+myelin sheath diameter)). The G ratio of intact axons is 0.5-0.8. Since the myelin sheath is thinner in remyelinated axons, an axon with a G ratio >0.8 was considered remyelinated.

Immunofluorescent staining of uncommitted Neural precursors in vitro and in vivo: The following primary antibodies were used: Rabbit IgG anti GFP (1:100, Chemicon), mouse IgG anti human specific mitochondria (1:200, Chemicon), mouse IgM anti-A2B5 (1:1, ATCC), mouse IgM anti PSA-NCAM (1:200, Chemicon), rabbit IgG anti-nestin (1:50, Chemicon), rabbit anti musashi (1:100, Chemicon), Anti human NUC, rabbit IgG anti-NG2 (1:50, Chemicon), mouse IgM anti-PDGFRα(1:20, R&D), rabbit IgG anti NGN2 (1:300, Chemicon), rabbit anti-galactocerebroside (GalC, 1:20, Chemicon), mouse IgM anti-O4 (1:20, Chemicon), rabbit IgG anti MAP2 (1:200, Chemicon), mouse IgG anti β tubulin III (1:2000, Sigma) rabbit anti-glial fibrillary acidic protein (GFAP, 1:100, Dako), rabbit IgG anti olig1 (1:20, Chemicon) and goat anti olig2 (1:30, R&D). Texas red or Alexa 488-conjugated goat anti-mouse IgM (1:100, Jackson, West Grove, PN), goat anti-rabbit IgG (1:100, Molecular Probes), goat anti-mouse IgG (1:100, Molecular Probes) or donkey anti-goat IgG (1:200, Jackson, West Grove, PN) were used as secondary antibodies, where appropriate.

For in-vitro characterization of the cells that were generated for transplantation, small aggregates of cells were plated on poly-D-lysine (10 µg/ml) and fibronectin (5 µg/ml; both from Sigma) pre-coated cover slips in a central well plates in NPM without growth factors. Half of the cultures were fixated in 4% paraformaldehyde After 4 hours and stained for A2B5, nestin, Musashi and PSA-NCAM. The rest of the cultures were fixed after 7 days of differentiation, and stained for β tubulin III and GFAP. The cell surface markers NG2, O4, and GalC were stained in living cells followed by fixation in 4% paraformaldehyde. The cells were incubated with primary antibody for 45 min followed by 30 min incubation with a secondary antibody. Mounting medium containing 4V, 6-diamidino-2-phenylindole (DAPI; Vector, Burlingame, Calif.) was used for nuclei counter staining.

For characterization of the in-vivo location and differentiation of the transplanted cells, double immunofluorescent staining was performed on 6-8 µm axial frozen brain sections. The sections were incubated with primary antibody overnight at 4° C. followed by 50 min incubation with a secondary antibody at room temperature.

Images were taken by a fluorescent (Nikon E600, Kanagawa, Japan) or confocal microscope (Zeiss, Feldbach, Switzerland). Three hundred cells were scored within random fields at X1000 magnification using the Nikon E600 fluorescent microscope. The percentage of each cell phenotype was determined by dividing the number of positively stained cells by the total number of DAPI stained nuclei.

Co-cultures of hESC-derived uncommitted neural precursors and LNCs: Lymph nodes were excised from naïve mice. LNCs were cultured as single-cell suspensions, as described previously [20] with 2.5 µg/ml ConA or in control medium. Neural precursors were irradiated with 3,000 Rad for 1 minute and then added directly to the LNC culture medium with nonstimulated or stimulated LNCs ($10^5$ NPs/$2 \times 10^5$ LNCs)

In-vitro proliferation assay: The proliferation of LNCs after 72-hour incubation in-vitro was evaluated by means of a standard $^3$H-thymidine incorporation assay, as described previously (20), In all fluorescent activated cell sorter (FACS) experiments, cells were pre-coated with anti-mouse CD16/CD32 (BD Pharmingen,) to block unspecific binding, and T cells were identified by cell-surface labeling with APC-labeled anti-Thy1.2 (BD Pharmingen). All samples were analyzed in a FACSCalibur apparatus using the Cell Quest software (BD Biosciences, San Jose, Calif.). The proliferation of T cells obtained from naive mice was evaluated by FACS analysis for the incorporation of the cell division tracking dye 5(6)-carboxyfluorescein diacetate succinimidyl ester (CFSE), as described previously (21), For CFSE FACS analysis, LNCs were pulsed with 3 µM CFSE (Molecular Probes, Eugene, Oreg.) for 10 minutes, washed, and further cultured with or without ConA for 72 hours. CFSE-labeled, non-activated cells were used as control samples. The fraction of T cells that entered cell cycle was calculated by the formula:

$$\frac{\sum \frac{\text{total events in cycle } n}{2^n (\text{for } n \geq 1)}}{\sum \frac{\text{Total events in cycle } n}{2^n (\text{for } n \geq 0)}}$$

T-cell activation was analyzed by staining with PE-labeled anti-CD25 (Serotec, Bicestar, United Kingdom) for interleukin-2 receptor α (IL-2Rα).

Statistical analysis: Clinical evaluations of CEAE mice and quantification of the pathological features were performed by examiner, blinded to the experimental group. The results are presented as mean± SD. For comparison of clinical and pathological parameters between experimental and control groups, student's t-test was used. For analysis of the relationship between the inflammatory process and the tissue damage, regression analysis was used.

Derivation of enriched population of committed oligodendrocyte progenitor cells (OPCs): Initial neural differentiation of hESC was induced as described above for the derivation of enriched population of uncommitted neural precursors. Following two weeks of culturing of hESC clusters in NPM supplemented with noggin (700 ng/ml), and the oligodendroglial mitogens bFGF (20 ng/ml) and EGF (20 ng/ml), the cultures were treated with retinoic acid (RA) (sigma) (10 µM) to induce caudal specification of the neuralized cells. Following 7 days of RA treatment, cultures were propagated as floating spheres in the oligodendroglial specific, modified Sato medium [22] supplemented with the oligodendroglial mitogens bFGF (20 ng/ml), EGF (20 ng/ml) and PDGF-AA (50 ng/ml), and the oligodendroglial survival and maturation factors neurotrophine 3 (NT3) (5 ng/ml) and triiodothyronine (T3) (40 ng/ml).

To derive an expandable population of neural precursors enriched for oligodendroglial progenitors (committed), initial neuralization of hESCs was induced as above with or without noggin supplementation. After 2 weeks of culturing in NPM supplemented with mitogens +/−noggin the clusters were treated with RA (1-10 µM; preferably 1 µM) and the hedgehog agonist, Purmurphamine (Merck) (0.5-2 µM; preferably 0.5 µM) to induce ventral-caudal specification of the neuralized cells. Following 7-21 days, preferably 21 days of treatment, the cultures were further propagated for three to 20 more weeks as floating spheres in modified Sato medium supplemented with low concentrations of purmorphamine (0.2-0.5 µM; preferably 0.5 µM), bFGF (20 ng/ml), EGF (20 ng/ml), (NT3; 5 ng/ml) and ascorbic acid (200 nM). For final differentiation, the clusters were plated on poly-D-Lysine (10 µg/ml) and fibronectin (5 µg/ml) coated coverslips in modified Sato medium supplemented with NT3 (5 µg/ml), ascorbic acid (200 nM) T3 (40 ng/ml) IGF1 (10 ng/ml;) with or without Rock inhibitor (10 µM; Sigma) for 2-21 days.

Results:

Characterization of hESC-Derived Neural Progeny

To evaluate the therapeutic potential of transplanted hESC-derived neural progeny in the animal model of MS, uncommitted neural precursors were derived from hESC by culturing clusters of undifferentiated hESC in suspension in chemically defined medium suplamented with noggin, bFGF and EGF and after 3 weeks further propagated in the same medium without noggin supplementation. It was demonstrated that these neural precursors were multipotent and can give rise both in vivo and in vitro to progeny representing the three major neural lineages including neurons, astrocytes and oligodendrocytes.

Figure 1E:
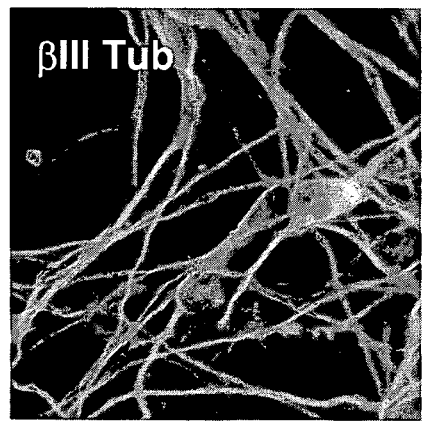
Figure 1F:
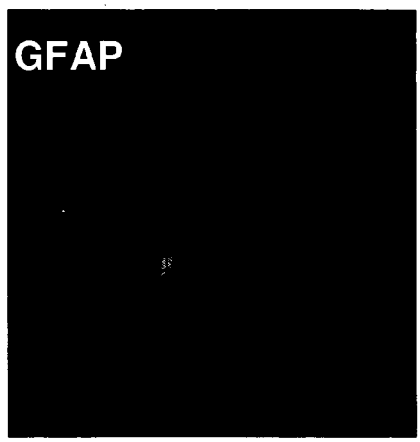

Prior to the transplantation of the hESC-derived neural precursors into the brain ventricles of chronic EAE rats, the characterization of their differentiation in vitro was once again established, which was consistent with previous published results [17]. Enriched populations of neural precursors in floating spheres were generated by culturing hESC clusters in serum free medium supplemented with noggin for 3 weeks. The spheres were further expanded 5 weeks in the same medium supplemented with mitogens (e.g. bFGF and EGF) before transplantation. The human neurospheres that were prepared for transplantation were highly enriched with uncommitted neural precursors, as indicated by the expression of A2B5, Musashi, nestin and PSA-NCAM (FIGS. 1A-1D, respectively). At this point differentiation of the neural precursors was induced by plating the spheres on fibronectin-coated coverslips and by mitogen withdrawal. Immunofluorescent staining, performed 7 days later, demonstrated that the neural precursors differentiated mainly into neurons and astrocytes, as was indicated by the expression of the neuronal marker βIII tubulin by 67% of the differentiating cells and the astrocyte marker GFAP by 12% of the cells (FIGS. 1E-1F). The expression of the oligodendroglial marker, O4 by differentiating cells, was marginal (<0.01%, not shown).

Figure 2:
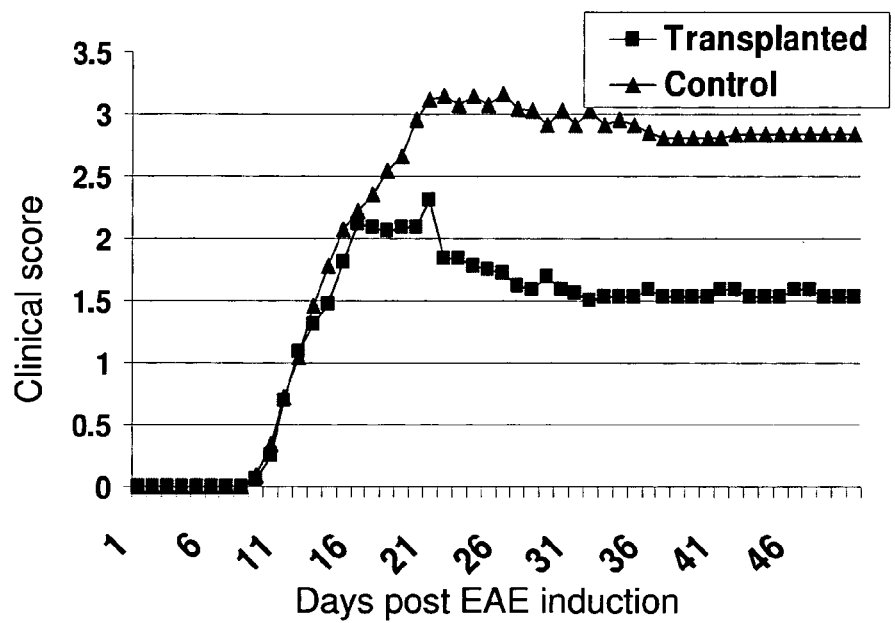
FIG. 2 is a graph showing a significant inhibition of the clinical parameters in transplanted animals (■) in comparison to control animals (▲) following transplantation of hESC-derived neural precursors.

The Effect of Transplanted hESC-Derived Uncommitted Neural Precursors on Clinical Course of EAE:

GFP expressing hESC-derived neural precursors were transplanted into the brain ventricles of chronic MOG EAE mice. As described in the Materials and Methods sections, the transplanted (n=15) and control (n=21) groups of MOG EAE mice were scored daily during a 38 days period for clinical signs of EAE (FIG. 2). Statistical analysis of the clinical scores revealed that transplanted hESC-derived NPs significantly attenuated the clinical signs of EAE, as was indicated by reduced maximal clinical scores and reduced cumulative scores in transplanted (■) versus control (▲) animals (FIG. 2 and Table 1). The severity of the disease was measured by calculating maximal clinical score, and cumulative clinical score (defined in the notes below([1,2])), for transplanted and control groups. Both clinical parameters of transplanted animals were significantly improved in comparison to controls. It is noted that reduced clinical signs in transplanted animals were evident as early as the acute phase of the disease.

TABLE 1

Parameters of EAE severity in transplanted and control animals

|  | cells transplanted (N = 15) | Control (N = 21) | P value |
|---|---|---|---|
| Max clinical score[1] | 2.65 ± 1.32 | 3.95 ± 1.25 | 0.0044 |
| Cumulative clinical score[2] | 58.06 ± 53.57 | 93.89 ± 51.58 | 0.0475 |

[1] Maximal clinical score = Mean of the maximal clinical scores during the experimental period.
[2] Cumulative clinical score = Mean of the sum of the daily clinical scores during the experimental period.

In-Vivo Localization and Differentiation Fate of Transplanted hESC-Derived Neural Precursors:

After the 38 days period of the behavioral follow up (described above), the transplanted and control animals were sacrificed for histopathological analysis. Immunofluorescent staining of brain sections demonstrated that the transplanted neural precursors, identified by the expression of human-specific mitochondria (FIGS. 3A, 3C-3G),/human nuclei antigens (FIG. 3B) or by expression of GFP (FIGS. 3A (insert), 3H) survived in the brain tissue.

Figure 3A:
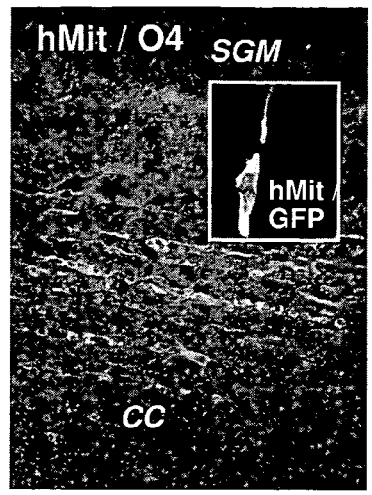
Figure 3B:
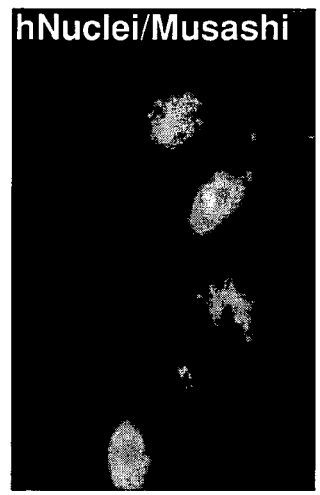
Figure 3C:
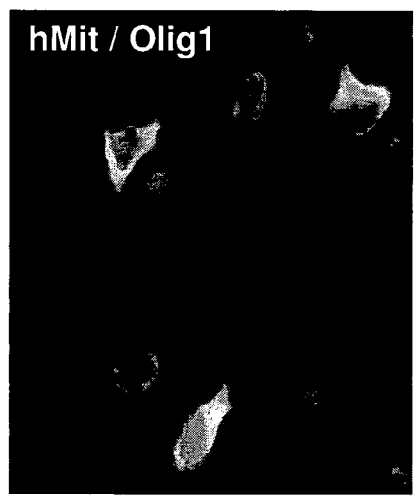

The neural precursors migrated extensively from the brain lateral ventricles exclusively into white matter areas such as the corpus callosum and the periventricular white matter (CC in FIG. 3A) and were not observed in grey matter areas such as subcortical grey matter (SGM in FIG. 3A). Costaining with anti-O4 which is an oligodendroglial marker, was used to identify the white matter (FIG. 3A). Nuclei were counterstained with DAPI. The high migratory properties of hESCs-derived neural precursors in response to inflammation is believed to be central to any beneficial effect of transplanted cells whether by their own regenerative potential or by reducing the disease process in their local surrounding.

Figure 3D:
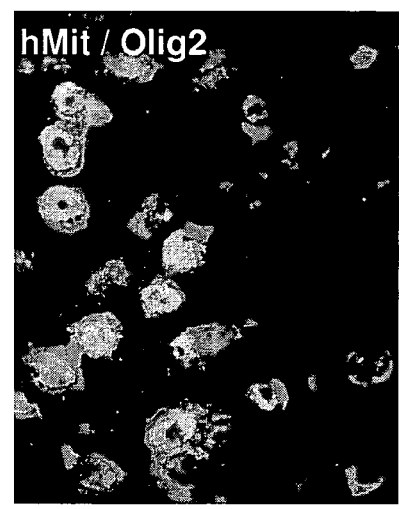
Figure 3E:
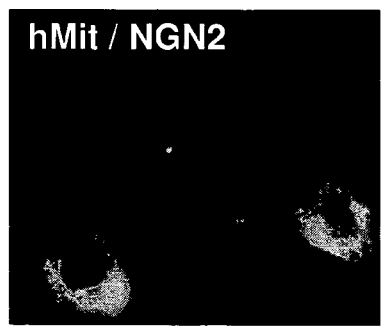
Figure 3F:

Immunofluorescent stainings demonstrated that most of the transplanted cells either remained as uncommitted precursors, identified by the expression of the RNA binding protein, Musashi (FIG. 3B) or committed into common bipotential neuronal/oligodendroglial precursors, expressing the bHLH transcription factors Olig1 (FIG. 3C) and Olig2 (FIG. 3D). Some transplanted cells further differentiated into neuronal precursors expressing NGN2 (FIG. 3E), oligodendroglial progenitors, expressing NG2 (FIG. 3F), astrocytes expressing GFAP (FIG. 3G) and mature oligodendrocytes expressing markers such as GalC (FIG. 3H). The incidence of differentiation into these cell types was ~1% per cell type.

Serial H&E-stained sections covering the entire brain did not reveal teratomas or any other tumor formation in transplanted mice.

These data showed that the transplanted hESC-derived neural precursors had the potential to undergo differentiation in vivo towards several cell types including oligodendrocytes and therefore they may be used for regeneration and remyelination in MS. However, the use in these studies, of an experimental animal model which allows only very limited remyelination, and consequently the relatively small amount of differentiation into mature oligodendrocytes highlighted that mechanisms other than remyelination by the transplanted cells may underline the observed therapeutic effect in this specific model.

Figure 3I:
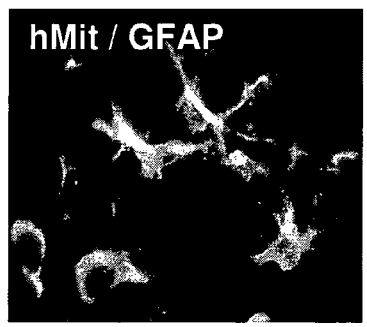
Figure 3I:
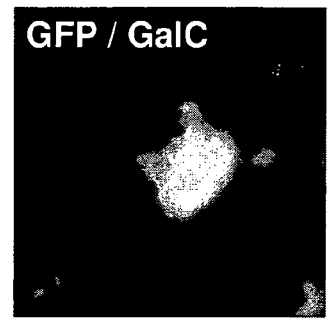
Figure 3I:
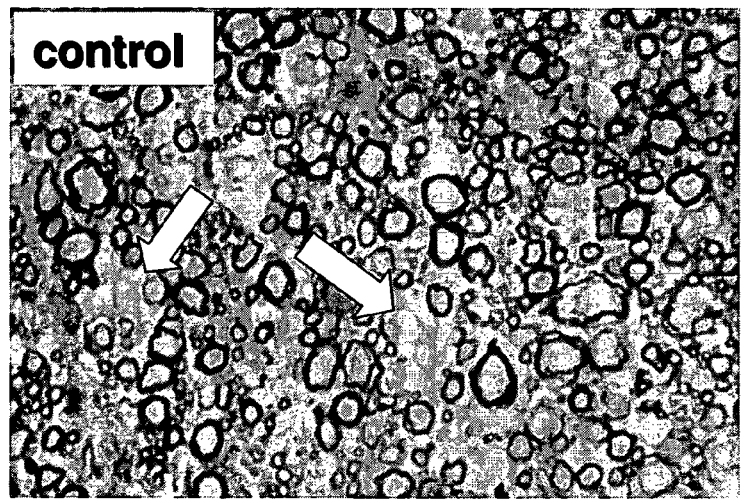
Figure 3J:
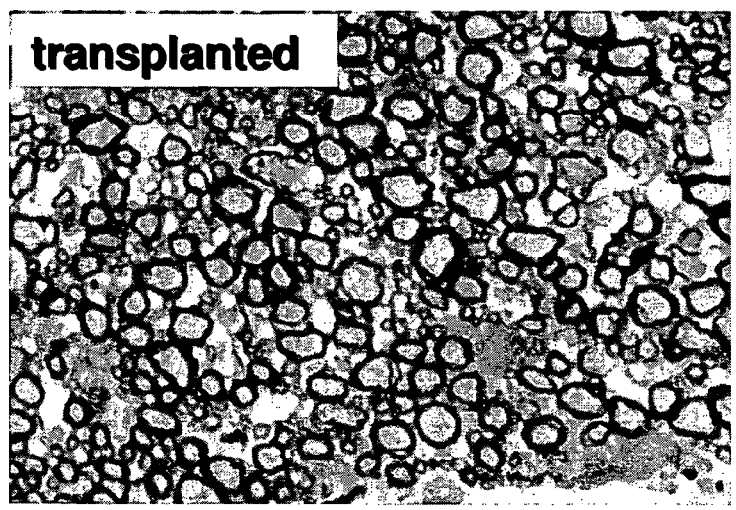

To determine whether transplantation had an effect on endogenous remyelination we calculated the G ratios of axons from toluidine blue stained spinal cord semi-thin sections. Axons with a G ratio >0.8 were considered remyelinated. Analysis of the G ratios values of axons from the transplanted and control groups revealed more demyelinated axons in the non-transplanted group (FIGS. 3I-3J) and a number of remyelinated axons in both groups (FIGS. 3I-3J). Albeit low remyelination, it is believed that subject to specific conditions selected, local transplantation of hESC-derived neural precursors (committed and/or uncommitted) will result in a meaningful remyelination preferably to an extent at least as equal to the protective anti-inflammatory effect obtained thereby or above (see below).

Transplanted hESC-Derived Neural Precursors Attenuate the Inflammatory Process and the Progression of Host Tissue Damage A time course experiment was performed in which the evolution of the inflammatory process and the tissue damage was compared in neural precursor-transplanted and control EAE mice. Following the induction of MOG EAE and transplantation as described above, mice from transplanted and control groups were sacrificed at 4 time points which represented 4 critical stages in the course of EAE: Day 10 in which immune cells begin to infiltrate the CNS although the disease does not yet manifest clinically; Day 13 in which there are early clinical signs and inflammation is more robust; Day 20 which represents the peak of the acute phase of MOG EAE; and Day 50 which represents the chronic phase. In each time point (n=5 per time point) histochemical and pathological analysis of spinal cord sections was performed to quantify the severity of inflammation, demyelination and axonal damage.

To measure the extent of inflammation, the numbers of immune cell infiltrations, numbers of CD3+ T cells and numbers of Mac3+ macrophages/activated microglia per mm$^2$ of the sections were examined. Demyelination and axonal injury were measured by luxol fast blue loss and Bielschowsky staining, respectively.

Figure 4:
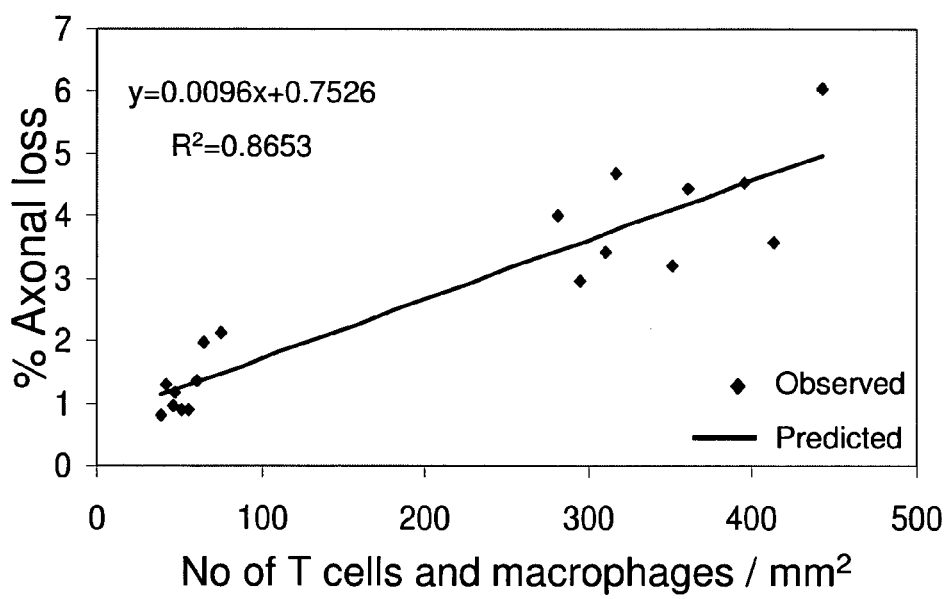
FIG. 4 provides linear regression analysis of neural precursors transplanted and control mice at 13 and 20 days post EAE induction showing in both groups in the acute phase of EAE a strong correlation between the numbers of T cells and macrophages per mm$^2$ and the percentage of axonal loss. ($r^2$=0.86, P=0.00002).

Regression analysis of T cells and macrophages the areas of axonal loss at days 13 and 20 post EAE induction demonstrated that in both transplanted and control groups the extent of the inflammatory process was strongly correlated to the severity of tissue damage at these time points ($r^2$=0.86, P=0.00002, FIG. 4). An evidence for initial infiltration of immune cells into the CNS was detected in both groups as early as 10 days post EAE induction. However, the numbers of CD3+ cells and Mac3+ cells were significantly decreased in the transplanted animals, starting from Day 13 and Day 20 post EAE induction, respectively (FIGS. 5A, 5D, 5G, and Table 2). The difference between the groups in the numbers of immune cells in the CNS even increased at the later time points examined (Table 2). In addition, axonal damage and demyeliantion were first detected in both groups at day 13 post induction (FIGS. 5J, 5M and Table 2). Both parameters became significantly reduced in the transplanted group as compared to the controls at day 20 post induction and the difference between the groups in the amount of axonal damage even increased at the last time point we examined (FIGS. 5J, and 5M, and Table 2). To summarize, FIGS. 5A-5O show that in neural precursors-transplanted mice an attenuation of the inflammatory process, indicated by less immune-cell infiltrates (FIG. 5A), less T cells (FIG. 5D) and less macrophages/activated microglia (FIG. 5G) was evident from Day 13 post EAE induction and became significant from Day 20 and on. Demyelination, indicated by loss of Kluver Barrera staining (FIG. 5J) and axonal damage, indicated by Bielschowsky staining (FIG. 5M) were both significantly reduced from Day 20 post EAE induction and on. Representative images of H&E staining FIGS. 5B, 5C), CD3 (FIGS. 5E, 5F) and Mac3 immunostaining (FIGS. 5H-5I), Kluver Barrera staining (FIGS. 5K-5L) and Bielschowsky silver staining (FIGS. 5N-5O) taken from Day 20 post EAE induction, demonstrate the reduction in transplanted versus control mice in the numbers of immune cell infiltrates, T cells, macrophages, areas of demyelination and areas of axonal damage, respectively.

Quantification of apoptotic CD3+ T cells in the histopathological sections showed 3.2±2.4% pyknotic T cell nuclei in control EAE CNS and 2.7±2.5% in transplanted CNS.

Thus, the effect of transplantation was not mediated by induction of T-cell apoptosis in the CNS of EAE mice. This determination supports the understanding that the neural progenitors provide a protective effect (by preventing immune cells from penetrating the CNS) and that there is no induction of apoptosis of immune cells in the CNS.

in a dose dependent manner (FIG. 6A). A maximal effect of 91% inhibition in 3H-thymidine incorporation was obtained when NPs/LNC ratio of 1:2 was used. This ratio was therefore used for the following in-vitro experiments.

The effect of hESC-derived neural precursors on T-cell activation and proliferation was then investigated. To this end, the induction of IL-2Rα, a marker for T-cell activation, in Thy1.2+ T cells was measured. In LNCs co-cultured with the human neural precursors the fraction of IL-2Rα T cells was reduced by 32%, and a similar decrease was observed in the mean fluorescence intensity of IL-2Rα (FIGS. 6B-6C). In addition, naive LNCs were labeled with CFSE and stimulated with ConA in the presence or absence of neural precursors. FACS analysis showed that the human

TABLE 2

Histopathological analyses of inflammatory parameters, demyelination, and axonal damage in the spinal cord of C57BL/6 mice at 10, 13, 20, and 30 days after MOG35-55 EAE induction

| Pathological parameter | | Control EAE (n = 5) | Transplanted (n = 5) | P Value |
|---|---|---|---|---|
| Inflammation | | | | |
| No. Immune cell infiltrations mm² (H&E) | Day 10 p.i.* | 0.18 ± 0.2 | 0.1 ± 0.13 | 0.5 |
| | Day 13 p.i.* | 1.43 ± 0.5 | 1.15 ± 0.4 | 0.32 |
| | Day 20 p.i.* | 7.1 ± 1.4 | 5.22 ± 0.6 | 0.044 |
| | Day 50 p.i.* | 5.1 ± 0.9 | 2.41 ± 0.7 | 0.006 |
| No. CD3 + T Cells/ mm² | Day 10 p.i.* | 2.5 ± 2.9 | 1.66 ± 2.3 | 0.65 |
| | Day 13 p.i.* | 19.16 ± 4.2 | 14.66 ± 4.3 | 0.047 |
| | Day 20 p.i.*0 | 152.9 ± 22.7 | 120.2 ± 11.1 | 0.016 |
| | Day 50 p.i.* | 108.05 ± 20.9 | 57.26 ± 13 | 0.029 |
| No. MAC3 + Macrophages/ mm² | Day 10 p.i.* | 4.79 ± 6 | 3.5 ± 4.8 | 0.73 |
| | Day 13 p.i.* | 40.2 ± 8.5 | 34.16 ± 5.8 | 0.24 |
| | Day 20 p.i.* | 240 ± 32.9 | 190 ± 19.8 | 0.027 |
| | Day 50 p.i.* | 179.44 ± 15.9 | 106.04 ± 22.5 | 0.005 |
| Axonal Pathology | | | | |
| % Axonal injury/Section (Bielschowsky) | Day 10 p.i.* | 0 | 0 | — |
| | Day 13 p.i.* | 1.3 ± 0.57 | 1.23 ± 0.53 | 0.758 |
| | Day 20 p.i.* | 4.65 ± 1 | 3.41 ± 0.4 | 0.038 |
| | Day 50 p.i.* | 5.22 ± 0.83 | 3.58 ± 0.25 | 0.024 |
| Demyelination | | | | |
| % Demyelination/ Section (Klyver Barrera - PAS) | Day 10 p.i.* | 0 | 0 | — |
| | Day 13 p.i.* | 0.68 ± 0.15 | 0.6 ± 0.14 | 0.409 |
| | Day 20 p.i.* | 4.2 ± 0.36 | 2.82 ± 0.5 | 0.002 |
| | Day 50 p.i.* | 4.36 ± 0.24 | 2.85 ± 1.4 | 0.002 |

*post injection

The above data demonstrated the potential of the hESC-derived neural precursors to differentiate in vivo towards the oligodendroglial fate and the potential of the transplanted hESC-derived neural precursors to attenuate the inflammatory process and consequently the host neural parenchymal pathology of EAE mice.

hESC-Derived Neural Precursors Inhibit Activation and Proliferation of Lymph-Node Cells, in Response to Concavalin A (ConA).

It was previously demonstrated that neural precursors derived from brains of newborn mice exhibited a bystander inhibitory effect on T-cell activation and proliferation in vitro (13). In order to determine whether the hESC-derived neural precursors have similar immunosuppressive properties, the neural precursors were co-cultured with lymph-node cells (LNCs). First, the ³H-thymidine incorporation assay was employed to test whether hESC-derived NPs exert a direct suppressor effect on the in-vitro proliferation of LNCs obtained from naïve C57BL mice. The human neural precursors inhibited LNC proliferation in response to ConA, neural precursors reduced the fraction of cycling T cells from 49% to 21% (FIG. 6D-6E).

Figure 7A:
FIGS. 7A-7I are fluorescent images showing oligodendroglial differentiation of hESCs in vitro following retinoic acid treatment, exhibited by expression of the (oligodendrocyte precursor cells) OPCs markers NG2 (12%) (FIGS. 7A,7C, 7D,7F) GD3 (20%) (FIGS. 7B, 7C) and PDGFRα (15%) (FIGS. 7E, 7F), as well as of the mature oligodendrocyte markers, O4 (FIGS. 7G, 7I) and GalC (FIGS. 7H, 7I). Nuclei in FIGS. 7C, 7F, 7G-7I are counter stained with DAPI.
Figure 7B:
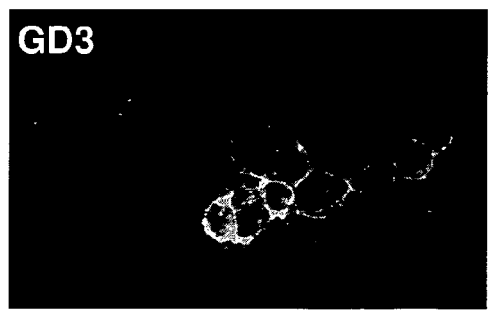
Figure 7C:
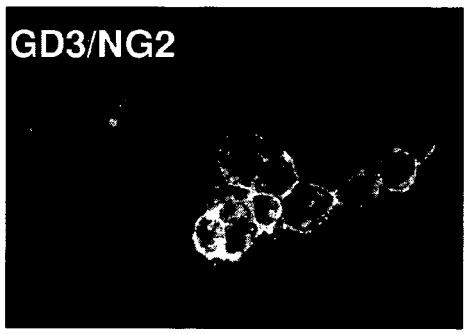
Figure 7D:
Figure 7E:
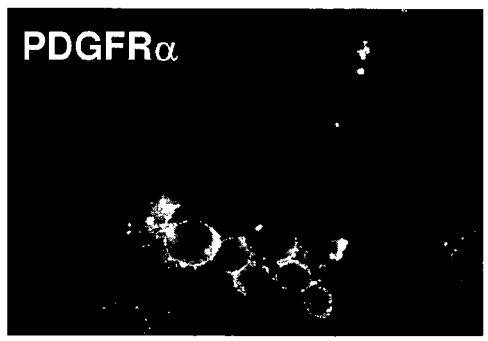
Figure 7F:
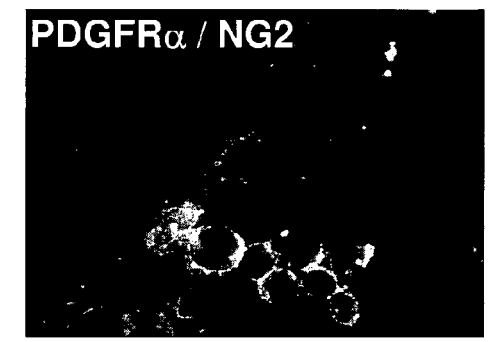
Figure 7G:
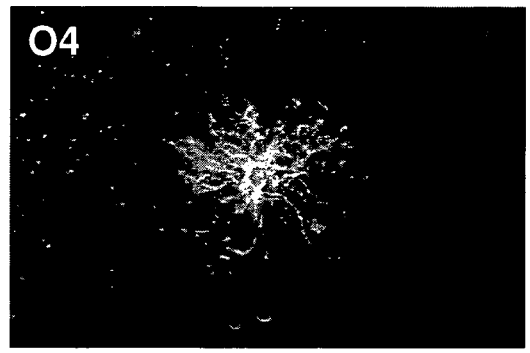
Figure 7H:
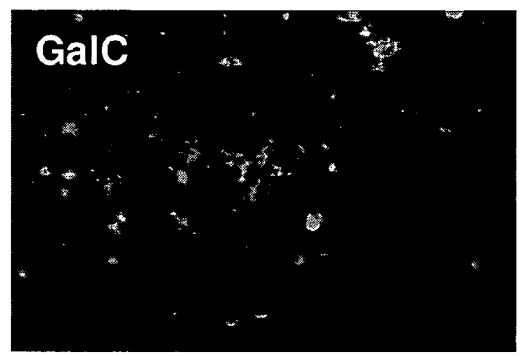
Figure 7I:
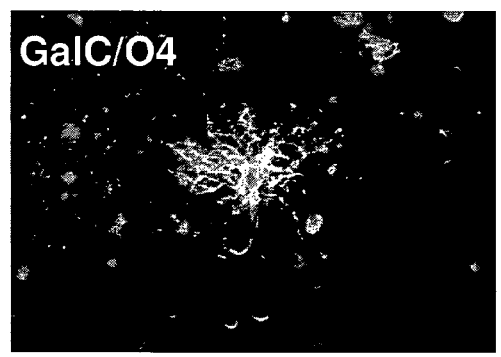

In vitro oligodendroglial differentiation of hESCs was examined. The experimental protocol included initial induction of human ESCs to differentiate as free floating clusters, under defined culture conditions, in the presence of noggin into early multipotent neural precursors according to the published protocols [17] as described above. After two weeks, they were treated with retinoic acid (RA) and propagated as floating spheres in modified Sato medium and mitogens At sequential week intervals, differentiation was induced by plating on fibronectin and withdrawal of the mitogens, and the expression of oligodendroglial markers were analyzed by immunostaining. After three weeks of propagation as free floating clusters, followed by plating and differentiation for 48 hours, the differentiating cells expressed the oligodendroglial markers NG2 (12%) (FIGS. 7A,6C, 7D, 7F) GD3 (20%) (FIGS. 7B, 7C) and PDGFRα (15%) (FIGS. 7E, 7F). Although at this stage of three weeks propagation, when enrichment for OPCs was obtained, markers of mature oligodendrocytes such as O4 and GalC were not detected, even after 7-10 days of differentiation. Only in cultures that were propagated for more than 5 weeks and induced to differentiate for 7 days, O4 and GalC were expressed by 3% and 1% of differentiating cells, respectively (FIGS. 7G, 7I (O4) and FIGS. 7H, 7I (GalC). Nuclei in FIGS. 7C, 7F, 7G-7I were counter stained with DAPI.

To develop expandable cultures enriched for oligodendroglial committed progenitors, hESCs clusters were induced to differentiate as free floating clusters into multipotent uncommitted neural precursors as above with or without noggin. After two weeks of initial neural induction the multipotent uncommitted neural precursors were further cultured for 1-3 weeks, preferably 3 weeks, as floating spheres in modified Sato medium supplemented with mitogens, retinoic acid (RA) and the hedgehog (HH) agonist purmorphamine. During this culture period the early multipotent neural precursors gradually become enriched with Olig2+ oligodendroglial precursors (30-50% of total cells).

Figure 8A:
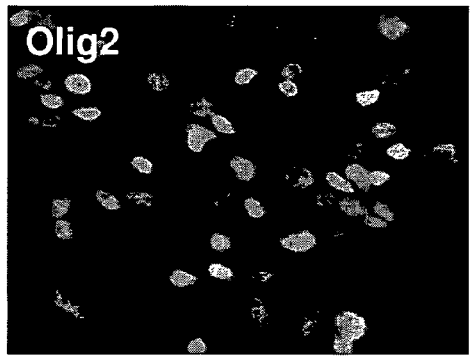
FIG. 8A-8H are fluorescence images of oligodendroglial differentiation of hESCs in vitro following treatment with retinoic acid and purmorphamine and propagation in low purmorphamine concentrations, as exhibited by expression of the OPCs markers Olig2 (30%) (FIG. 8A), PDGFRα (20%) (FIG. 8B) and NG2 (20%) (FIG. 8C) as well as markers of mature oligodendrocytes O4 (20%) (FIG. 8D), GalC (15%) (FIG. 8E) and MBP (3%) (FIG. 8F), as well as the expression of Olig2 (FIG. 8G) and O4 (FIG. 8H) in the absence of low purmorphamine concentrations
Figure 8B:
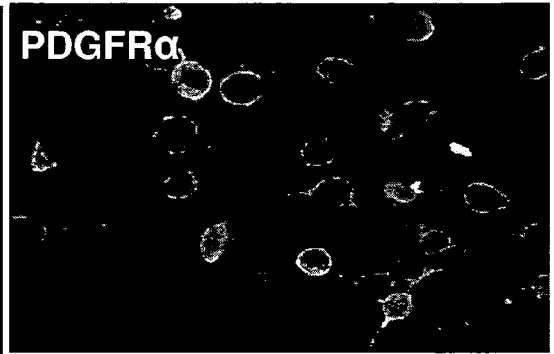
Figure 8C:
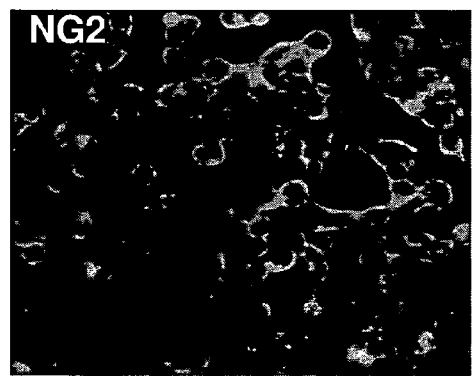
Figure 8D:
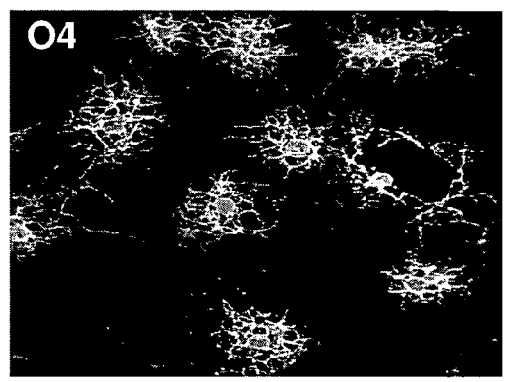
Figure 8E:
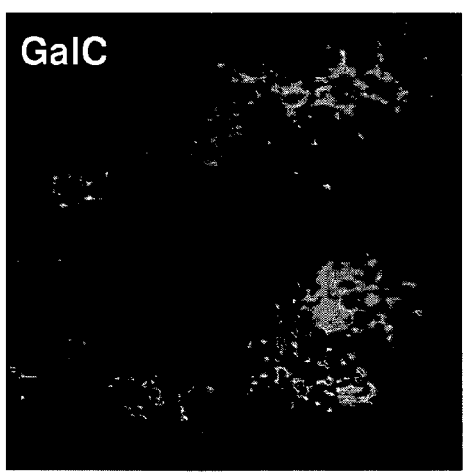
Figure 8F:
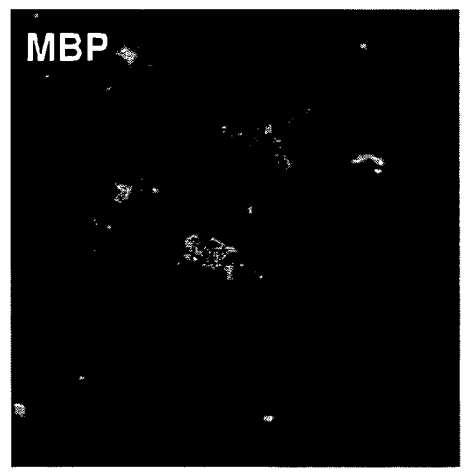

For further expansion of the oligodendroglial precursors, the floating spheres were propagated in Sato medium supplemented with mitogens, and low concentrations (0.5 μM) of purmorphamine. After 3-20 weeks of propagation as free floating clusters and plating on fibronectin for 24-48 hours, expression of the OPC markers Olig2 (FIG. 8A), PDGFRα (FIG. 8B) and NG2 (FIG. 8C) were detected in 30%, 20% and 20% of the differentiating cells, respectively. Following further 7-21 days of differentiation in the presence of NT3, AA, T3 and IGF1 +/− Rock inhibitor, markers of mature oligodendrocytes such as O4 (FIG. 8D), GalC (FIG. 8E) and MBP (FIG. 8F) were detected in 20%, 15% and 3% of the plated cells, respectively.

Figure 8G:
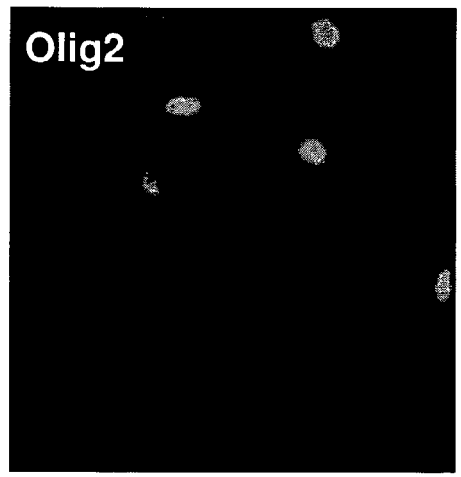
Figure 8H:

In cultures where early neutralization (2 weeks) and caudal ventral specification with RA and HH agonist (3 weeks) was induced as above but were further propagated in Sato medium in the absence of purmorphamine the level of enrichment for Olig2 and O4 following five weeks of propagation and 1-7 days of differentiation was only 5% and 3%, respectively (FIGS. 8G-8H).

Taking into consideration all the above results, it was concluded that transplantation of hESC-derived neural precursors in any manner, to patients suffering from autoimmune demyelination disease, e.g. MS, may facilitate both remyelination and attenuation of the local inflammatory process and thus produce a dual therapeutic effect. Such oligodendroglial-committed precursors may also be transplanted in combination with hESC-derived multipotent, non oligodendroglial-committed precursors, to obtain neural protection and regeneration by each of the two neural precursor types respectively.

REFERENCE

1. Reubinoff, B. E., et al., *Embryonic stem cell lines from human blastocysts: somatic differentiation in vitro*. Nat Biotechnol, 2000. 18(4): p. 399-404.
2. Thomson, J. A., et al., *Embryonic stem cell lines derived from human blastocysts*. Science, 1998. 282(5391): p. 1145-7.
3. Brustle, O., et al., *Embryonic stem cell-derived glial precursors: a source of myelinating transplants*. Science, 1999. 285(5428): p. 754-6.
4. Keirstead, H. S., et al., *Human embryonic stem cell-derived oligodendrocyte progenitor cell transplants remyelinate and restore locomotion after spinal cord injury*. J Neurosci, 2005. 25(19): p. 4694-705.
5. Liu, S., et al., *Embryonic stem cells differentiate into oligodendrocytes and myelinate in culture and after spinal cord transplantation*. Proc Natl Acad Sci USA, 2000. 97(11): p. 6126-31.
6. Zhang, P. L., et al., *Increased myelinating capacity of embryonic stem cell derived oligodendrocyte precursors after treatment by interleukin-6/soluble interleukin-6 receptor fusion protein*. Mol Cell Neurosci, 2006. 31(3): p. 387-98.
7. Kang, S. M., et al., *Efficient Induction of Oligodendrocytes from Human Embryonic Stem Cells*. Stem Cells, 2006.
8. Glaser, T., et al., *Generation of purified oligodendrocyte progenitors from embryonic stem cells*. Faseb J, 2005. 19(1): p. 112-4.
9. Liu, S., et al., *Embryonic stem cells differentiate into oligodendrocytes and myelinate in culture and after spinal cord transplantation*. Proc Natl Acad Sci USA, 2000. 97(11): p. 6126-31.
10. Perez-Bouza, A., T. Glaser, and O. Brustle, *ES cell-derived glial precursors contribute to remyelination in acutely demyelinated spinal cord lesions*. Brain Pathol, 2005. 15(3): p. 208-16.
11. Nistor, G. I., et al., *Human embryonic stem cells differentiate into oligodendrocytes in high purity and myelinate after spinal cord transplantation*. Glia, 2005. 49(3): p. 385-96.
12. Einstein, O., et al., *Transplanted neural precursor cells reduce brain inflammation to attenuate chronic experimental autoimmune encephalomyelitis*. Exp Neurol, 2006. 198(2): p. 275-84.
13. Einstein O., et al., *Neural precursors attenuate autoimmune encephalomyelitis by peripheral immunosuppression*. Ann Neurol (2007). 61: p. 209-218.
14. Pluchino, S., et al., *Neurosphere-derived multipotent precursors promote neuroprotection by an immunomodulatory mechanism*. Nature, 2005. 436(7048): p. 266-71.
15. Pluchino, S., et al., *Injection of adult neurospheres induces recovery in a chronic model of multiple sclerosis*. Nature, 2003. 422(6933): p. 688-94.
16. Shin, S., et al., *Whole genome analysis of human neural stem cells derived from embryonic stem cells and stem and progenitor cells isolated from fetal tissue*. Stem cells (2007). 25(5): p. 1298-306
17. 18. Itsykson, P., et al., *Derivation of neural precursors from human embryonic stem cells in the presence of noggin*. Mol Cell Neurosci, 2005. 30(1): p. 24-36.
18. Ben-Dor, I., *Lentiviral vectors harboring a dual-gene system allow high and homogeneous transgene expression in selected polyclonal human embryonic stem cells*. Mol Ther (2006).14: p. 255-267.
19. Gropp, M., et al. *Stable genetic modification of human embryonic stem cells by lentiviral vectors*. Mol Ther (2003) 7:p. 281-287.
20. Einstein, O., et al., *Intraventricular transplantation of neural precursor cell spheres attenuates acute experimental allergic encephalomyelitis*. Mol Cell Neurosci, 2003. 24(4): p. 1074-82.
21. Bronstein-Sitton N., et al., *Sustained exposure to bacterial antigen induces interferon-gamma dependent T cell receptor zeta down-regulation and impaired T cell function*. Nat Immunol, 2003. 10: p. 957-64.
22. Billon, N., et al., *Normal timing of oligodendrocyte development from genetically engineered, lineage-selectable mouse ES cells*. J Cell Sci, 2002. 115(Pt 18): p. 3657-65.
23. US patent application publication No. US 2005/0282272

The invention claimed is:

1. A method, comprising:
preparing an expandable population of neural precursor cells committed to an oligodendroglial fate,
wherein the expandable population of neural precursor cells committed to the oligodendroglial fate expresses oligodendrocyte transcription factor (Olig2) and platelet-derived growth factor receptor (PDGFRα), and at least one marker selected from the group consisting of ganglioside 3(GD3) and neural/glial antigen 2(NG2); and
wherein the preparation of the expandable population of neural precursor cells committed to an oligodendroglial fate comprises:
incubating early multipotent uncommitted neural precursor cells derived from human pluripotent stem cells in a first medium comprising retinoic acid (RA) and a first concentration between 0.5 µM and 2 µM of a hedgehog (HH) agonist, allowing the early multipotent uncommitted neural precursor cells to propagate as floating spheres; and
incubating the floating spheres for at least three weeks in a second medium supplemented with a second concentration of HH agonist that is not more than 0.5 µM and with at least one mitogen selected from the group consisting of basic fibroblast growth factor (bFGF), epidermal growth factor (EGF), and platelet-derived growth factor (PDGF), wherein the second medium does not comprise RA, to obtain the expandable population of the neural precursor cells committed to the oligodendroglial fate,
wherein the expandable population of neural precursor cells committed to the oligodendroglial fate express Olig2 and PDGFRα, and at least one marker selected from the group consisting of GD3 and NG2.

2. The method of claim 1, comprising plating the obtained expandable population of neural precursor cells committed to an oligodendroglial fate on an extracellular matrix (ECM) whereby differentiation of the expandable population of neural precursor cells committed to an oligodendroglial fate to terminally differentiated oligodendrocytes is obtained.

3. The method of claim 2, wherein the plating is performed in the absence of HH agonist and in the absence of a mitogen.

4. The method of claim 2, wherein the extracellular matrix is fibronectin.

5. The method of claim 1, wherein the HH agonist is purmorphamine.

6. The method of claim 1, wherein the first concentration of HH agonist is 0.5 µM, and the second concentration of HH agonist is between 0.2 µM and 0.5 µM.

7. The method of claim 1,
wherein the expandable population of neural precursor cells committed to the oligodendroglial fate comprises: 30% of the neural precursor cells expressing Olig2, 20% of the neural precursor cells expressing PDGFRα, and 20% of the neural precursor cells expressing NG2, and
wherein the expandable neural precursor cells committed to the oligodendroglial fate can be further differentiated into a cellular population comprising oligodendrocytes, wherein the cellular population comprises 20% expression of marker 4(O4), 15% expression of galactocerebroside (GalC), and 3% expression myelin basic protein (MBP).

8. A method, comprising
preparing an expandable population of neural precursor cells committed towards an oligodendroglial fate,
wherein the expandable population of neural precursor cells committed to the oligodendroglial fate expresses oligodendrocyte transcription factor (Olig2) and platelet-derived growth factor receptor (PDGFRα), and at least one marker selected from the group consisting of ganglioside 3(GD3) and neural/glial antigen 2(NG2); and
wherein the preparation of the expandable population of neural precursor cells committed to an oligodendroglial fate comprises:
incubating early multipotent uncommitted neural precursor cells derived from human pluripotent stem cells a first medium comprising retinoic acid (RA) and a first concentration between 0.5 µM and 2 µM of a hedgehog (HH) agonist, allowing the early multipotent uncommitted neural precursor cells to propagate as floating spheres; and
incubating the floating spheres for at least three weeks in a second medium supplemented with a second concentration of HH agonist that is not more than 0.5 µM, wherein the second medium does not comprise RA, to obtain the expandable population of the neural precursor cells committed to the oligodendroglial fate,
wherein the expandable population of neural precursor cells committed to the oligodendroglial fate express Olig2 and PDGFRα, and at least one marker selected from the group consisting of NG2 and GD3.

9. The method of claim 8, wherein the HH agonist is purmorphamine.

10. The method of claim 8, wherein the first concentration of HH agonist is 0.5 μM, and the second concentration of HH agonist is between 0.2 μM and 0.5 μM.

11. A method for preparing an expandable population of neural precursor cells committed to an oligodendroglial fate, the method comprising:
   incubating early multipotent uncommitted neural precursor cells derived from human pluripotent stem cells in a first medium comprising retinoic acid (RA) and a first concentration between 0.5 μM and 2 μM of a hedgehog (HH) agonist, allowing the early multipotent uncommitted neural precursor cells to propagate as floating spheres; and
   incubating the floating spheres for at least three weeks in a second medium consisting of a second concentration of HH agonist that is not more than 0.5 μM and optionally, at least one of neurotrophine 3 (NT3), triiodothyronine (T3), or a mitogen, wherein the mitogen is basic fibroblast growth factor (bFGF), epidermal growth factor (EGF), or platelet-derived growth factor (PDGF), to obtain the expandable population of the neural precursor cells committed to the oligodendroglial fate,
   wherein the expandable population of neural precursor cells committed to the oligodendroglial fate expresses cyte transcription factor (Olig2) and platelet-derived growth factor receptor (PDGFRα), and at least one marker selected from the group consisting of ganglioside 3(GD3) and neural/glial antigen 2(NG2).

12. A method for preparing an expandable population of neural precursor cells committed towards an oligodendroglial fate,
   the method comprising:
   incubating early multipotent uncommitted neural precursor cells derived from human pluripotent stem cells in a first medium comprising retinoic acid (RA) and a first concentration between 0.5 μM and 2 μM of a hedgehog (HH) agonist, allowing the early multipotent uncommitted neural precursor cells to propagate as floating spheres; and
   incubating the floating spheres for at least three weeks in a second medium consisting of a second concentration of HH agonist that is not more than 0.5μM and optionally, at least one of neurotrophine 3(NT3) or triiodothyronine (T3) to obtain the expandable population of the neural precursor cells committed to the oligodendroglial fate,
   wherein the expandable population of neural precursor cells committed to the oligodendroglial fate express oligodendrocyte transcription factor (Olig2) and platelet-derived growth factor receptor (PDGFRα), and at least one marker selected from the group consisting of ganglioside 3(GD3) and neural/glial antigen 2(NG2).

* * * * *

UNITED STATES PATENT AND TRADEMARK OFFICE
CERTIFICATE OF CORRECTION

PATENT NO. : 9,862,925 B2
APPLICATION NO. : 12/740496
DATED : January 9, 2018
INVENTOR(S) : Michal Aharonowiz et al.

Page 1 of 1

It is certified that error appears in the above-identified patent and that said Letters Patent is hereby corrected as shown below:

In the Claims

In Claim 8, Column 24, Line 50, insert --in-- after "pluripotent stem cells".
In Claim 11, Column 25, Line 26, delete "cyte" and replace with "oligodendrocyte".

Signed and Sealed this
Twenty-eighth Day of May, 2019

Andrei Iancu
*Director of the United States Patent and Trademark Office*